(12) United States Patent
Sheardown et al.

(10) Patent No.: US 12,403,197 B2
(45) Date of Patent: Sep. 2, 2025

(54) POLYMER SYSTEM FOR OPHTHALMIC DRUG DELIVERY

(71) Applicant: McMaster University, Hamilton (CA)

(72) Inventors: Heather Sheardown, Hamilton (CA); Mitchell Ross, Hamilton (CA); Talena Rambarran, Hamilton (CA)

(73) Assignee: McMaster University, Hamilton (CA)

( * ) Notice: Subject to any disclaimer, the term of this patent is extended or adjusted under 35 U.S.C. 154(b) by 109 days.

(21) Appl. No.: 17/546,645

(22) Filed: Dec. 9, 2021

(65) Prior Publication Data

US 2022/0175932 A1    Jun. 9, 2022

Related U.S. Application Data

(60) Provisional application No. 63/123,173, filed on Dec. 9, 2020.

(51) Int. Cl.
| | | |
|---|---|---|
| A61K 47/36 | (2006.01) | |
| A61K 9/06 | (2006.01) | |
| A61K 47/32 | (2006.01) | |
| C08G 81/02 | (2006.01) | |
| G02B 1/04 | (2006.01) | |

(52) U.S. Cl.
CPC ............... *A61K 47/36* (2013.01); *A61K 9/06* (2013.01); *A61K 47/32* (2013.01); *C08G 81/02* (2013.01); *G02B 1/043* (2013.01)

(58) Field of Classification Search
CPC ......... A61K 47/32; A61K 47/36; C08L 33/26; C08L 33/02
See application file for complete search history.

(56) References Cited

U.S. PATENT DOCUMENTS

| | | | | |
|---|---|---|---|---|
| 2004/0156880 A1* | 8/2004 | Ravi | ........................ | A61L 27/50 623/5.14 |
| 2010/0316715 A1* | 12/2010 | Andersson | ............... | A61L 27/20 435/395 |
| 2016/0258856 A1* | 9/2016 | Kim | .................... | G01N 15/1012 |
| 2020/0360282 A1* | 11/2020 | Fedorchak | ............... | A61K 9/06 |

FOREIGN PATENT DOCUMENTS

| | | | |
|---|---|---|---|
| CN | 100341899 C | 4/2006 | |
| WO | WO-2019099630 A1 * | 5/2019 | ........... A61K 31/573 |

OTHER PUBLICATIONS

Barbu et al (Nanotechnology, vol. 20, 2009, pp. 1-10) (Year: 2009).*
Morones-Ramirez (Brazilian Journal of Chemical Engineering, vol. 27, 2010, pp. 1-14) (Year: 2010).*
Yu et al., 2012, "Synthesis and Characterization of Temperature-Sensitive Poly(N-isopropylacryamide) Hydrogel with Comonomer and Semi-IPN Material", Polymer-Plastics Technology and Engineering, vol. 51, pp. 854-860.
Saitoh et al., 2009, "Chitosan-Conjugated Thermo-Responsive Polymer for the Rapid Removal of Phenol in Water", Reactive & Functional Polymers, vol. 69, pp. 792-796.
Rasib et al., 2018, "Synthesis and Evaluation of pH- and Temperature-Responsive Chitosan-p(MAA-co-NIPAM) Hydrogels", International Journal of Biological Macromolecules, vol. 108, pp. 367-375.
Okudan et al., 2019, "Investigation of the Effects of Different Hydrophilic and Hydrophobic Comonomers on the Volume Phase Transition Temperatures and Thermal Properties of N-Isopropylacrylamide-Based Hydrogels", International Journal of Polymer Science, vol. 2019, pp. 1-13.
Luo et al., 2018, "Effect of Deacetylation Degree on Controlled Pilocarpine Release from Injectable Chitosan-g-poly(N-isopropylacrylamide) Carriers", Carbohydrate Polymers, vol. 197, pp. 375-384.
Lai et al., 2017, "Chitosan-g-poly(N-isopropylacrylamide) Copolymers as Delivery Carriers for Intracameral Pilocarpine Administration", European Journal of Pharmaceutics and Biopharmaceutics, vol. 113, pp. 140-148.
Cao et al., 2007, "Poly(N-isopropylacrylamide)-chitosan as Thermosensitive in Situ Gel-Forming System for Ocular Drug Delivery", Journal of Controlled Release, vol. 120, pp. 186-194.
Yimia et al., 2018, "Chitosan-Based In Situ Gels for Ocular Delivery of Therapeutics: A State-of-the-Art Review," Mar Drugs, vol. 16, pp. 1-23.
Luo, et al., 2018, "Effect of deacetylation degree on controlled pilocarpine release from injectable chitosan-g-poly(N-isopropylacrylamide) carriers," Carbohydr Polym, vol. 197, pp. 375-384.
Sacco et al., 2018, "Concepts for Developing Physical Gels of Chitosan and of Chitosan Derivatives," Gels, vol. 4, pp. 1-29.
Cheng et al., 2016, "Thermosensitive chitosan-based hydrogel as a topical ocular drug delivery system of latanoprost for glaucoma treatment," Carbohydr Polym, vol. 144, pp. 390-399.
Cui et al., 2011, "Degradation, cytotoxicity, and biocompatibility of NIPAAm-based thermosensitive, injectable, and bioresorbable polymer hydrogels," J Biomed Mater Res A, vol. 98, pp. 159-166.
Patenaude et al., 2012, "Injectable, Degradable Thermoresponsive Poly(N-isopropylacrylamide) Hydrogels," ACS Macro Letters, vol. 1, pp. 409-413.
Mazumder et al., 2012, "Cell-adhesive thermogelling PNIPAAm/hyaluronic acid cell delivery hydrogels for potential application as minimally invasive retinal therapeutics," Journal of biomedical materials research Part A, vol. 100, pp. 1877-1887, 2012.
Das et al., 2015, "Stimulus-Responsive, Biodegradable, Biocompatible, Covalently Cross-Linked Hydrogel Based on Dextrin and Poly(N-isopropylacrylamide) for in Vitro/in Vivo Controlled Drug Release," ACS Appl Mater Interfaces, vol. 7, pp. 14338-14351.

(Continued)

*Primary Examiner* — Mark V Stevens
(74) *Attorney, Agent, or Firm* — Smart & Biggar LP; Luba Naiberger

(57) ABSTRACT

This application relates to a thermo-gel polymer system useful for ophthalmic drug delivery. The thermo-gel comprises a polymer and chitosan, and the polymer comprises monomers of N-isopropylacrylamide (NIPAAm), acrylic acid (AA) and at least one hydrophobic monomer.

19 Claims, 26 Drawing Sheets

(56) References Cited

OTHER PUBLICATIONS

Lai, 2013, "Biodegradable in situ gelling delivery systems containing pilocarpine as new antiglaucoma formulations: effect of a mercaptoacetic acid/N-isopropylacrylamide molar ratio," Drug Design, Development and Therapy, vol. 7, pp. 1273-1285.

Yu et al., 2008, "Synthesis and characterization of thermoresponsive hydrogels cross-linked with chitosan," Central European Journal of Chemistry, vol. 6, pp. 107-113.

Yu et al., 2010, "Synthesis and characterization of temperature-sensitive and biodegradable hydrogel based on N-isopropylacrylamide," Central European Journal of Chemistry, vol. 8, pp. 426-433.

Lai et al., 2017, "Chitosan-g-poly(N-isopropylacrylamide) copolymers as delivery carriers for intracameral pilocarpine administration," Eur J Pharm Biopharm, vol. 113, pp. 140-148.

Boddupalli et al., 2010, "Mucoadhesive drug delivery system: An overview," Journal of advanced pharmaceutical technology & research, vol. 1, pp. 381-387.

Shaikh et al., 2011 "Mucoadhesive drug delivery systems," Journal of Pharmacy and Bioallied Sciences, vol. 3, pp. 89-100.

Zhu et al., 2004, "pH-dependent mucoadhesion of a poly(N-isopropylacrylamide) copolymer reveals design rules for drug delivery," Langmuir, vol. 20, pp. 10648-10656.

Cao et al., 2007, "Poly(N-isopropylacrylamide)-chitosan as thermosensitive in situ gel-forming system for ocular drug delivery," J Control Release, vol. 120, pp. 186-194.

Fedorchak et al., 2017, "Long term glaucoma drug delivery using a topically retained gel/microsphere eye drop," Scientific reports, vol. 7, pp. 1-11.

Saitoh et al., 2009, "Chitosan-conjugated thermo-responsive polymer for the rapid removal of phenol in water," Reactive and Functional Polymers, vol. 69, pp. 792-796.

Lue et al., 2011, "Tuning of Lower Critical Solution Temperature (LCST) of Poly(N-Isopropylacrylamide-co-Acrylic acid) Hydrogels," Journal of Macromolecular Science, Part B, vol. 50, pp. 563-579.

Okudan et al., 2019, "Investigation of the Effects of Different Hydrophilic and Hydrophobic Comonomers on the Volume Phase Transition Temperatures and Thermal Properties of N-Isopropylacrylamide-Based Hydrogels," International Journal of Polymer Science, pp. 1-12.

Jimenez et al., 2021, "A sustained release cysteamine microsphere/thermoresponsive gel eyedrop for corneal cystinosis improves drug stability," Drug Delivery and Translational Research, vol. 11, pp. 2224-2238.

Luo et al., 2020, "Long-acting mucoadhesive thermogels for improving topical treatments of dry eye disease," Materials Science and Engineering: C, vol. 115, pp. 1-14.

"Polymer Molecular Weight Distribution and Definitions of MW Averages", 2015, Agilent Technologies.

\* cited by examiner a)

b)

a)

b)

a)

b)

c)

a)

b)

a)

b)

POLYMER SYSTEM FOR OPHTHALMIC DRUG DELIVERY

CROSS-REFERENCE TO RELATED APPLICATIONS

The present application claims the benefit of priority from U.S. Provisional Patent Application No. 63/123,173 filed on Dec. 9, 2020, the contents of which are incorporated herein by reference in their entirety.

FIELD

The present application relates to polymer systems, and in particular, a thermo-gel polymer system for ophthalmic drug delivery.

BACKGROUND

Allergic conjunctivitis affects 36% of the US population [1]. Allergic conjunctivitis is an umbrella term used to refer to several hypersensitivity issues affecting the conjunctiva, eyelid and/or cornea [2]. Symptoms of allergic conjunctivitis include tearing, itching and conjunctival hyperemia. The treatment of anterior ocular conditions, such as allergic conjunctivitis, is commonly accomplished using topical eye drops and ointments which are easy to apply, cheap and non-invasive. It is generally accepted that with topical eye drops, less than 5% of an applied dose remains bioavailable after administration [3]. There are several barriers which limit the applied dosage including drainage by the nasolacrimal duct, rapid tear turnover and sources of undesirable absorption [4]. Topical eye drops are the most common treatment method of allergic conjunctivitis based on, for example, decongestants, antihistamines, mast cell stabilizers, nonsteroidal anti-inflammatory drugs (NSAID) and/or corticosteroid solutions [5]. According to the American Academy of Allergy, Asthma and Immunology, nearly all brand name topical eye drops for the treatment of allergic conjunctivitis require a minimum of one dose a day.

Chitosan based hydrogels have been tested as potential ocular therapies due to their biodegradability, biocompatibility, muco-adhesion, corneal wound healing effects and anti-microbial/fungal effects [6, 7]. Lysozyme is the highest concentration tear protein, at approximately 1.5 mg/mL, and can catalyze the hydrolysis of 1,4-β-linkages between the N-acetyl-D-glucosamine units of chitosan [8, 9]. Chitosan is the partially deacetylated form of chitin which consists of less than 50% of N-acetyl-D-glucosamine units. The degree of deacetylation (DDA) is a material property of chitosan that affects the enzymatic degradation rate by lysozyme along with the chitosan's molecular weight. The enzymatic rate is increased with lower DDA, between 50-75%, along with lower molecular weights [10-12]. Various sustained release ocular formulations based on chitosan have been developed including in situ gels, inserts, liposomes, microspheres/micelles and nanoparticles [13]. In situ gels at ambient conditions remain as polymeric solutions but collapse, by a tuneable sol-gel transition, into hydrogel networks by action of an external stimulus at physiological conditions. Ocular in situ forming gels based on chitosan generally fall into one of three categories; thermo-responsive, pH-responsive and ion-sensitive [6, 14]. Ocular, thermo-responsive, chitosan gels are typically based on the addition of polyol bearing compounds such as glycerophosphate with chitosan or by combining chitosan with thermo-sensitive synthetic monomers/polymers such as poloxamers or n-isopropylacrylamide (NIPAAm) [6, 14, 15].

Since its first usage in the 1980s, NIPAAm based hydrogels have been frequently used for biomedical applications [16, 17]. Poly(n-isopropylacrylamide) (pNIPAAm) hydrogels are defined by their reversible thermo-gelation around the lower critical solution temperature (LCST) of 32-35° C. The LCST of pNIPAAm based hydrogel systems can be either raised or lowered by inclusion of hydrophilic or hydrophobic comonomers respectively [17]. The degradation of pNIPAAm based hydrogels is typically accomplished through hydrolysis by the inclusion of various comonomers [18, 19]. pNIPAAm based hydrogels were previously developed incorporating dimethyl-γ-butyrolactone acrylate, which undergoes slow hydrolytic ring opening, allowing for degradation over multiple months. This system was used for posterior eye injection applications [20-23]. Other pNIPAAm based hydrogel systems have incorporated copolymers to allow for enzymatic degradation. Some examples include the incorporation of dextrin to pNIPAAm by the use of the crosslinker N,N'-methylene bis acrylamide which was enzymatically degraded by lysozyme [24] and gelatin which was grafted through covalent bonding by carbodiimide (EDC) conjugation and degraded by the collagenase enzyme MMP-2 or MMP-9 [25-27].

pNIPAAm has been grafted with chitosan for different applications in literature, the most common of which is hydrogel strengthening. Not all these systems are enzymatically degradable however, since the degradation of chitosan is heavily dependent on its material properties. pNIPAAm based hydrogels have been grafted with chitosan through EDC chemistry and have been shown to degrade via incubation with enzyme pepsin in simulated gastric fluid at 37° C. [28, 29]. As it pertains to ocular formulations, a similar system of chitosan grafted to pNIPAAm by EDC has been used as a platform for intracameral injections for the treatment of glaucoma. This system is enzymatically degraded when incubated with lysozyme, at the concentrations found in rabbit aqueous humour, at 34° C. [11, 30-32].

Mucin is another component of the tear film coating the surface of the eye acting as both a lubricator and barrier [33]. Studies have investigated using the mucus layers present throughout the body as anchorage points for drug eluting materials [34-37]. Mucoadhesive materials are often based on covalent conjugation, ionic interaction, hydrogen bonding, Van der Waals forces, mechanical interlocking and/or diffusion interpenetration [35, 38, 39]. Chitosan has been established to be mucoadhesive primarily through electrostatic interaction also accompanied by hydrophobic effects and hydrogen bonding [40]. Studies have investigated the development of mucoadhesive thermo-gels based on either pNIPAAm [41-43] or poloxamer blends [44-46]. Particularly, Sosnik et al., developed mucoadhesive micelles based on pNIPAAm blocks grafted to chitosan [42]. Recently, thiol bearing polymers/moieties have also been incorporated into mucoadhesive systems for disulfide bonding with the cysteine residues of mucin [47, 48]. Applications of drug delivery systems, for the treatment of anterior eye conditions, to the inferior fornix (also known as the cul-de-sac) have been reported in the literature as alternatives to conventional eye drops [49-51]. These developed hydrogel systems have the ability for sustained drug delivery offering a advantage over conventional, once daily, topical eye drops. Healthy patients blink on average 10-25 times per minute and the mechanical loading that blinking represents would cause rapid deterioration of any applied hydrogel scaffold directly to the eye surface [52]. Therefore, application to the inferior fornix has been investigated such that the developed hydrogels do not deteriorate as quickly during blinking or obstruct vision. These developed systems are typically either non-degradable in-situ gels, degradable pre-set films or ocular inserts. Ocular inserts due to their solid nature can often be uncomfortable for patients due to sensitivity of foreign bodies and along with pre-set films need to be placed accurately into the inferior fornix to avoid dislodging and unwanted migration. Therefore, there is a significant need for degradable thermo-gels that offer prolonged drug release, improved anchorage and simple application without the need for removal from the eye.

SUMMARY

The present application discloses a thermo-gel that, for example, allows for sustained release of a therapeutic agent. The thermo-gel degrades over time, and the degradation by-products are safely removed by the natural clearance mechanisms of the eye.

Therefore, the present application includes a thermo-gel comprising:
a) a polymer (pNAX), comprised of monomers of N (N-isopropylacrylamide (NIPAAm)), A (acrylic acid (AA)) and X (a hydrophobic monomer); and
b) chitosan,
wherein the chitosan is covalently or ionically bonded to the polymer In some embodiments, the chitosan is conjugated to the pNAX using 1-ethyl-3-(3-dimethyl aminopropyl)-carbodiimide (EDC).

In some embodiments, the polymer comprises 60-98.5 mol % NIPAAm, 1-10 mol % AA and 0.5-30 mol % of the hydrophobic monomer.

In some embodiments, the lower critical solution temperature (LCST) of the thermo-gel is slightly lower than physiological temperature, ideally below 37° C.

In some embodiments, the initial LCST of the polymer is lowered by the addition of the hydrophobic comonomer, allowing for more chitosan to be incorporated and yielding a crosslinked system with an ideal LCST for anterior ocular drug delivery. Controlling the amount of chitosan crosslinked into the system allows for control of the mechanical properties of the thermo gel which dictate the degradation and drug release profiles.

In some embodiments, acrylic acid is incorporated throughout the polymer, allowing for increased number of crosslinks of the polymer with chitosan through the crosslinker.

In some embodiments, the thermo-gel comprises up to 5 wt % chitosan with the chitosan having between 50-80 degree of deacetylation (DDA), and a molecular weight of 10-300 kDa.

In some embodiments, the thermo-gel is used for anterior ocular drug delivery, and is applied to the inferior fornix or cul-de-sac of the eye.

In some embodiments, the thermo-gel further comprises one or more therapeutic agents. In some embodiments, the one or more therapeutic agents are selected from drugs useful to treat ophthalmic conditions.

In some embodiments, the thermo-gel is used to treat ophthalmic conditions including, but not limited to, corneal healing, glaucoma, ophthalmic pain relief, glaucoma, allergic conjunctivitis, dry eye, cystinosis, infection, uveitis and/or post-surgical applications to increase healing. In further embodiments, the thermo-gel is used for additional applications including but not limited to contact lens materials, or transdermal drug delivery.

In some embodiments, a method of treating an ophthalmic condition is provided, comprising administering to a subject the thermo-gel containing a therapeutic amount of the therapeutic agent.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which.

Figure 10:
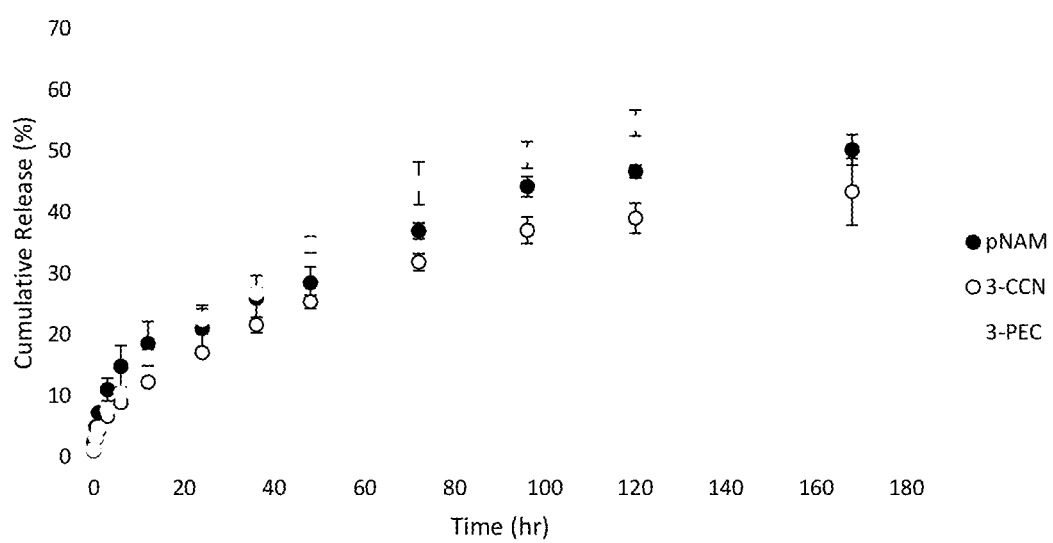
Figure 11:
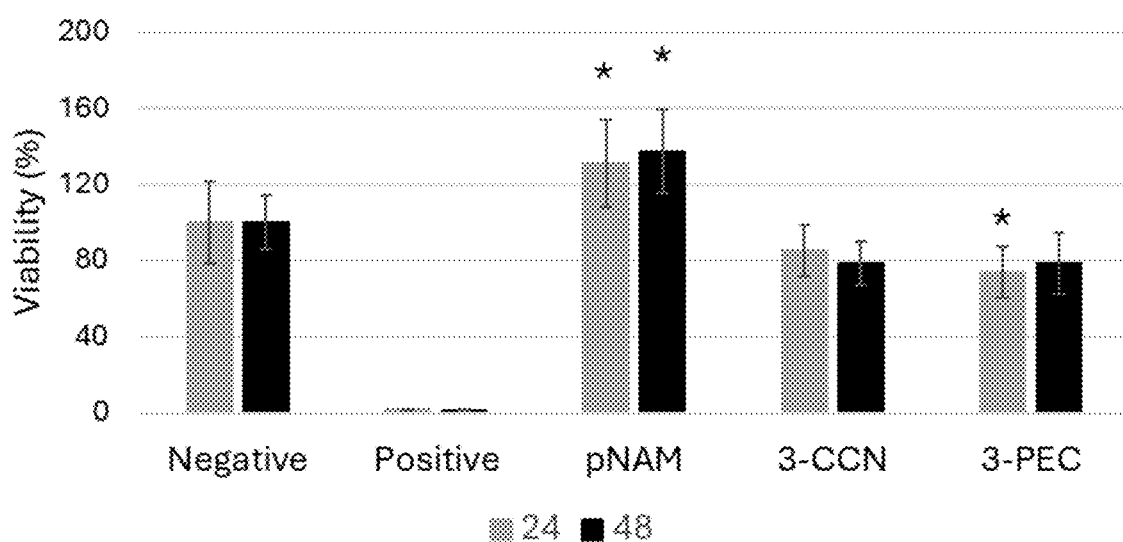

FIG. 10 shows the release of KF from pNAM, 3-CCN and 3-PEC thermo-gels over 7 days as measured by HPLC. 3-CCN gels release statistically less ($p<0.05$) Ketotifen Fumarate then 3-PEC and uncrosslinked pNAM at 5 days. Overall, 3-CCN releases less Ketotifen FIG. 11 shows results from the MTT cytotoxicity assay for the exemplary pNAM, 3-CCN and 3-PEC thermo-gels after 24 and 48 hours of incubation. Uncrosslinked pNAM gels produced a statistically higher ($p<0.05$) viability compared to positive control over 24 and 48 hours. 3-CCN gels were not statistically different from positive controls at 24 or 48 hours while 3-PEC performed just under positive control at 24 hours ($p=0.049$).

Figure 12:
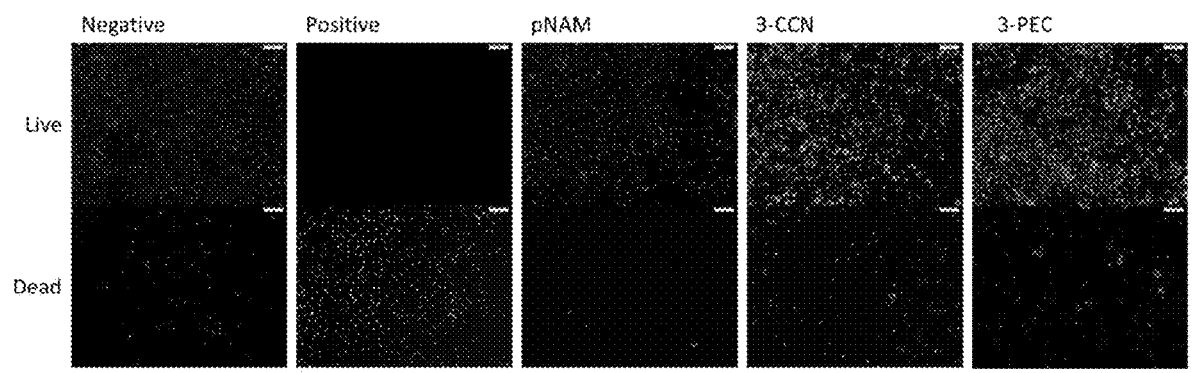

FIG. 12 shows histological H&E staining of Brown Norway Rat Corneas following 24-hour incubation with exeamplary pNAM, 3-CCN and 3-PEC thermo-gels. Top row 10× objective magnification, bottom row 20× objective magnification. No observable difference in corneal inflammation or morphology following short term thermo-gel treatment.

Figure 13:
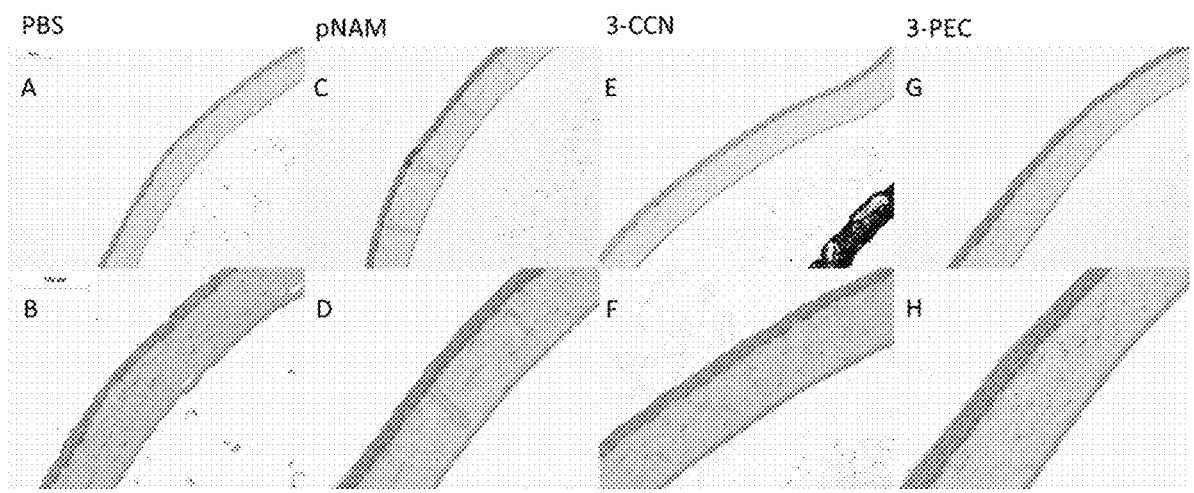

FIG. 13 shows histological staining of Brown Norway Rat Corneas following 24-hour incubation with exemplary pNAM, 3-CCN and 3-PEC thermo-gels. Top row 10× objective magnification, bottom row 20× objective magnification.

There was no observable difference in corneal inflammation or morphology following short term thermo-gel treatment.

Figure 14:
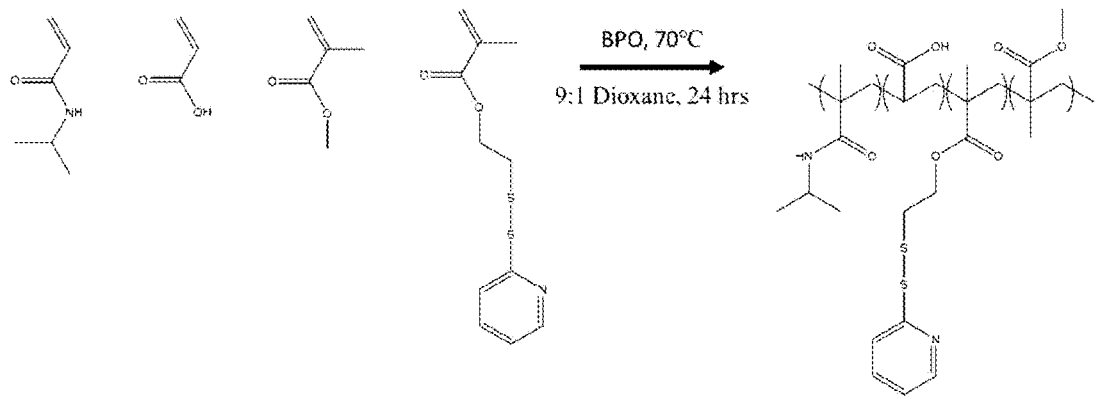
Figure 14:
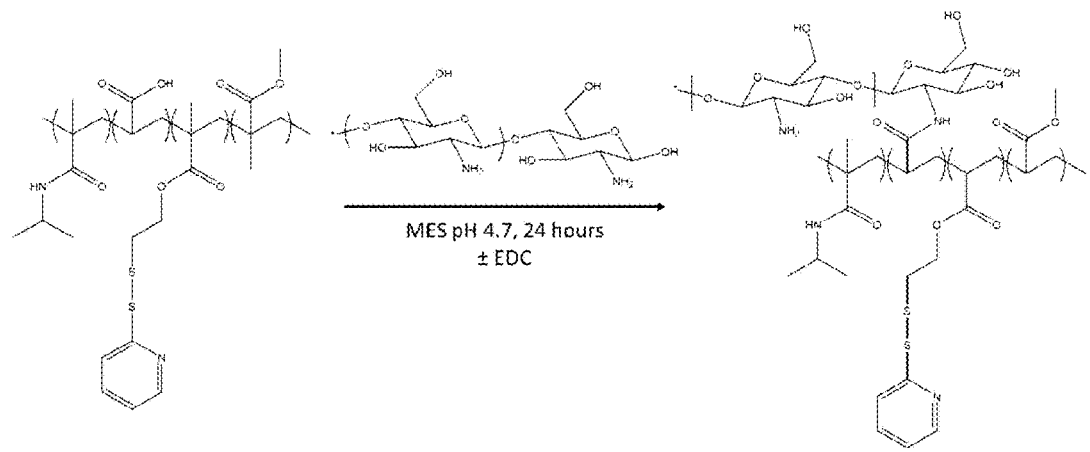
Figure 14:
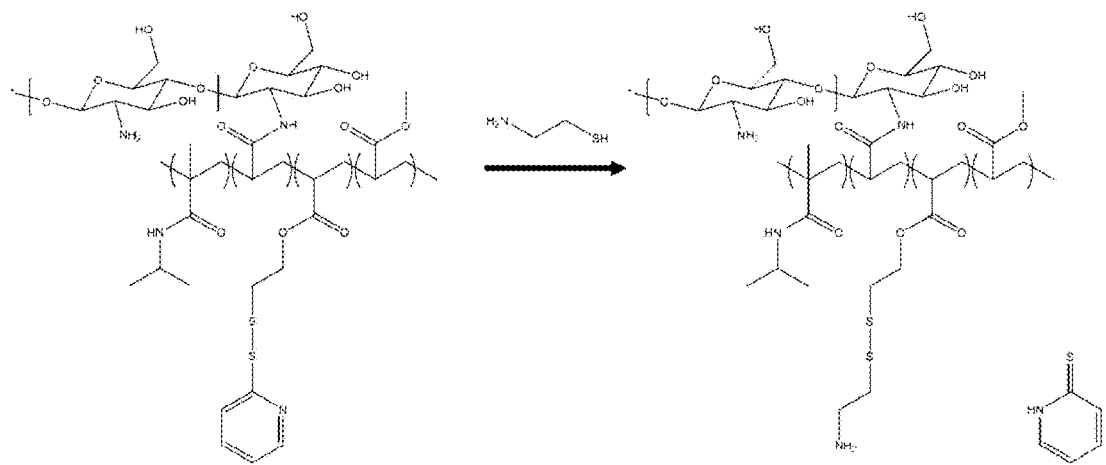
Figure 15:
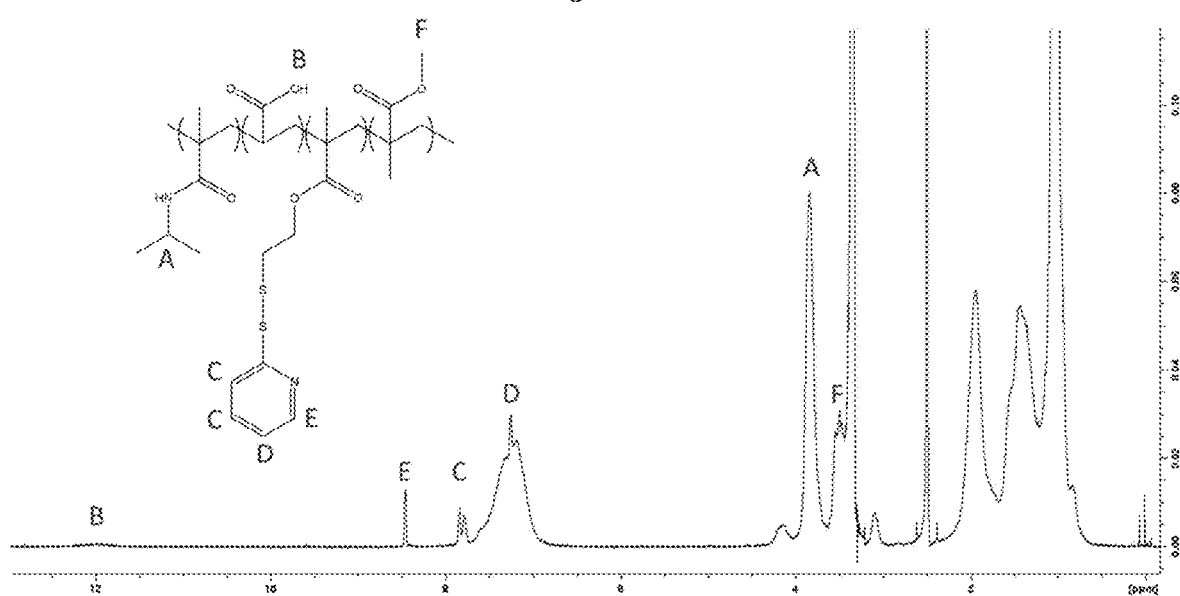

FIG. 14 a) shows a schematic of the free radical polymerization of exemplary pNAMP; and b) shows a schematic of the crosslinking of the exemplary pNAMP with chitosan; and c) shows a schematic of the conjugation of cysteamine to exemplary CTS-pNAM FIG. 15 shows the $^1$H NMR Analysis of the exemplary pNAMP polymer.

Figure 16:
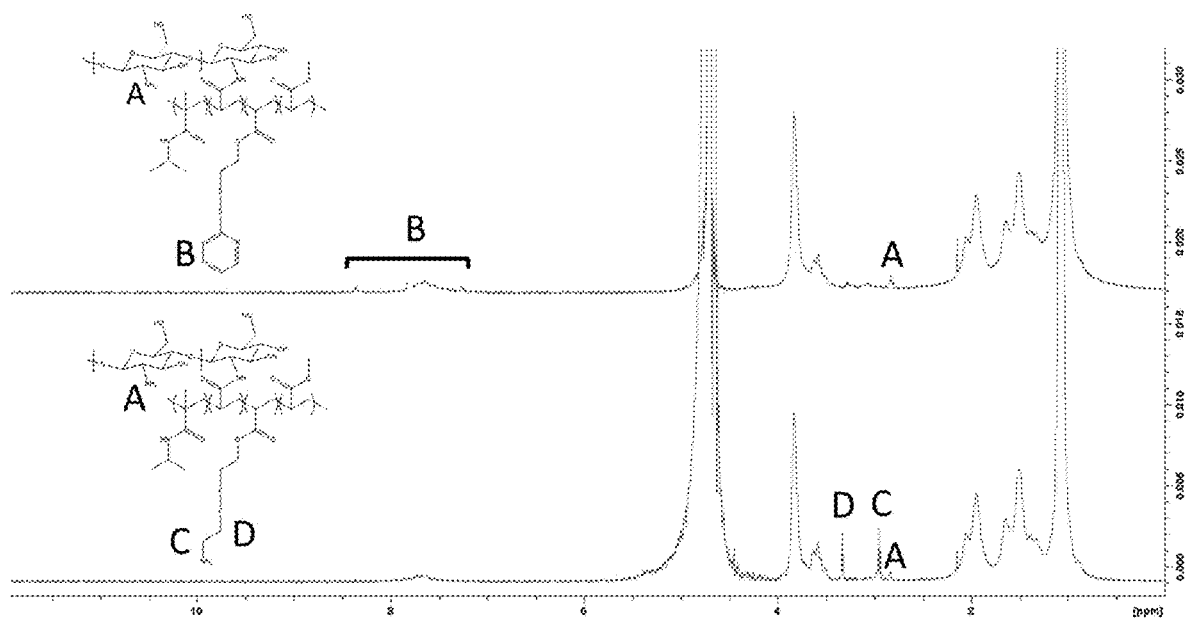

FIG. 16 shows the $^1$H NMR analysis of exemplary CTS-pNAMP-3 (top) and CTS-pNAMP-C3 (bottom).

Figure 17:
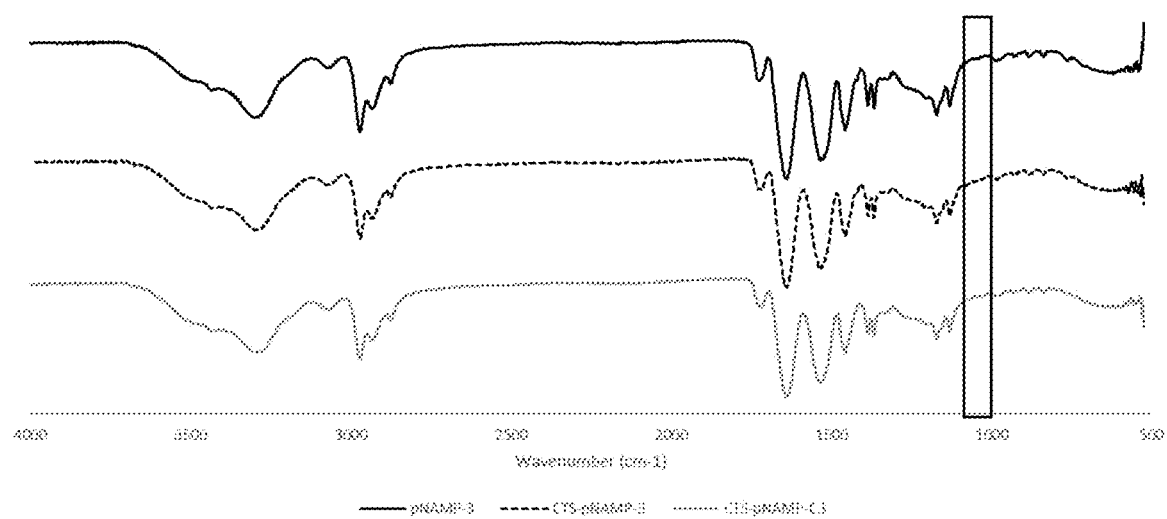

FIG. 17 shows the FTIR spectra of exemplary pNAMP-3, CTS-pNAMP-3 and CTS-pNAMP-C3.

Figure 18:
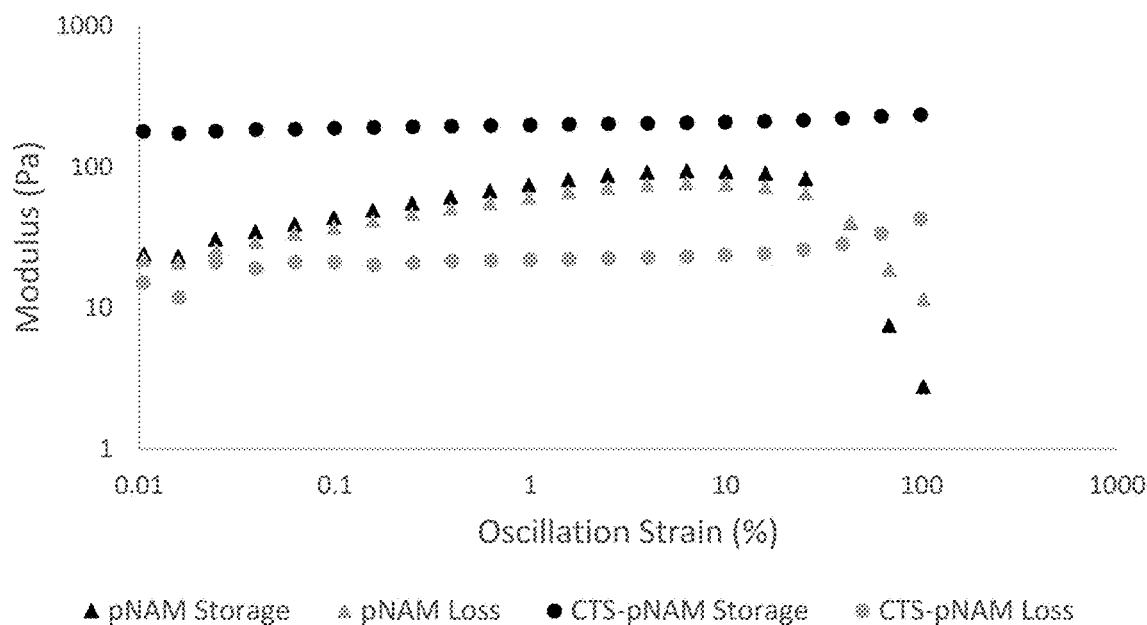
Figure 18:
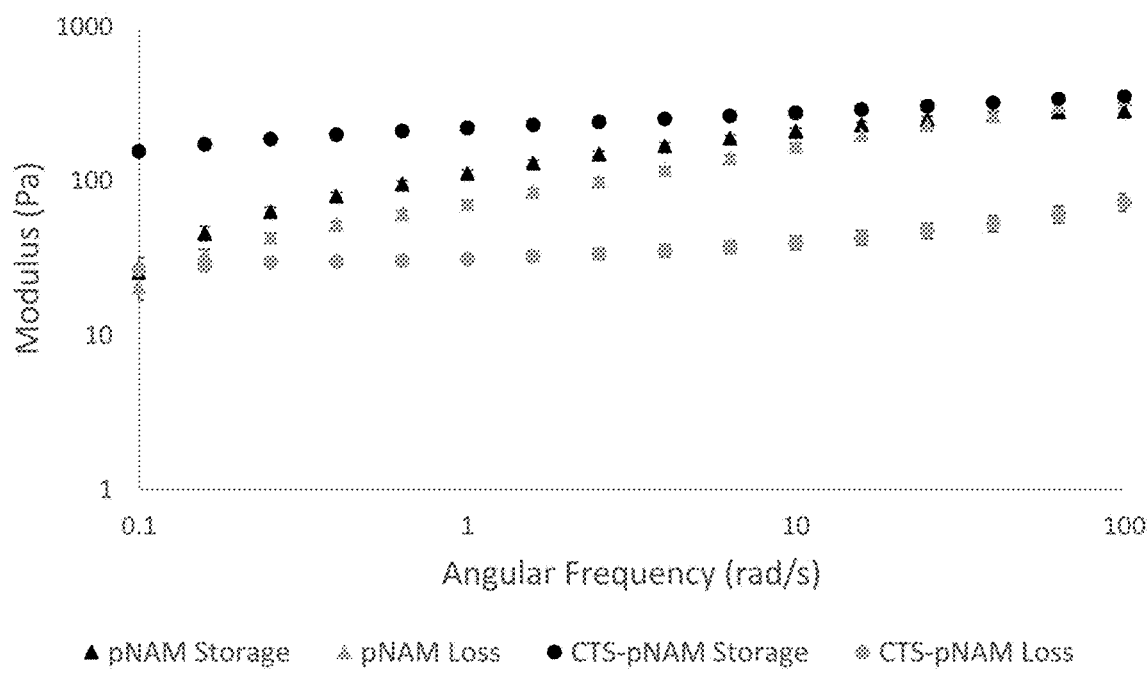
Figure 18:
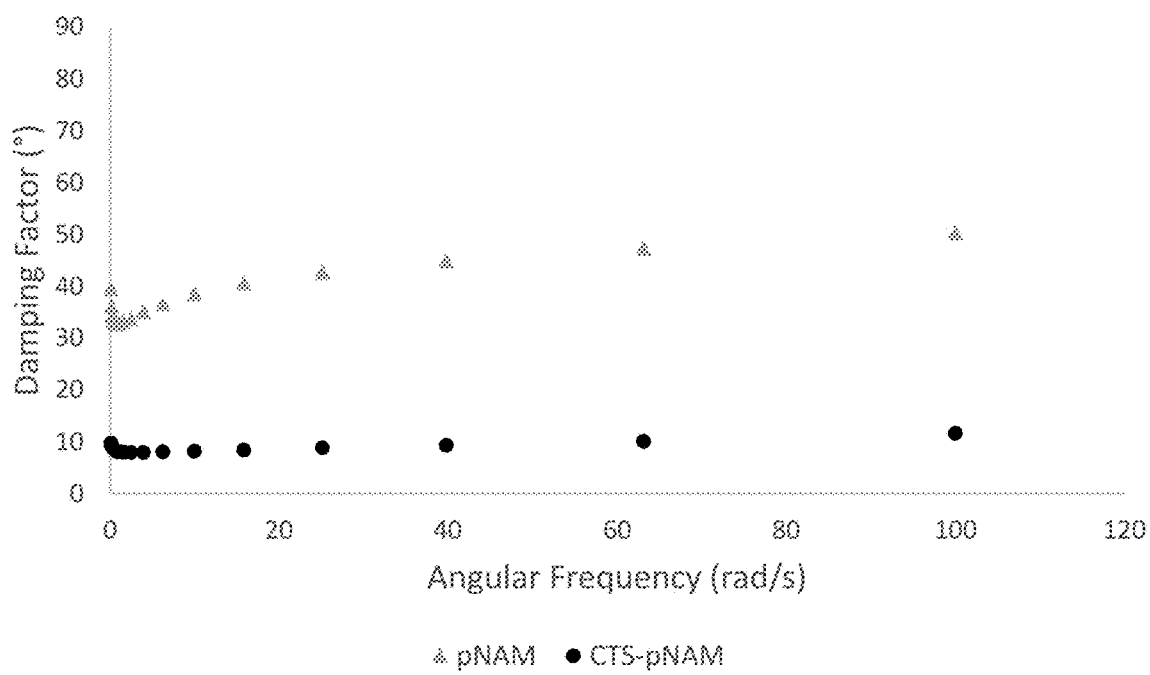

FIG. 18 a) shows the strain sweep analysis of exemplary pNAM and CTS-pNAM thermo-gels; b) frequency sweep analysis of exemplary pNAM and CTS-pNAM thermo-gels; and the damping factor for exemplary pNAM and CTS-pNAM thermo-gels calculated from the frequency sweep.

Figure 19:
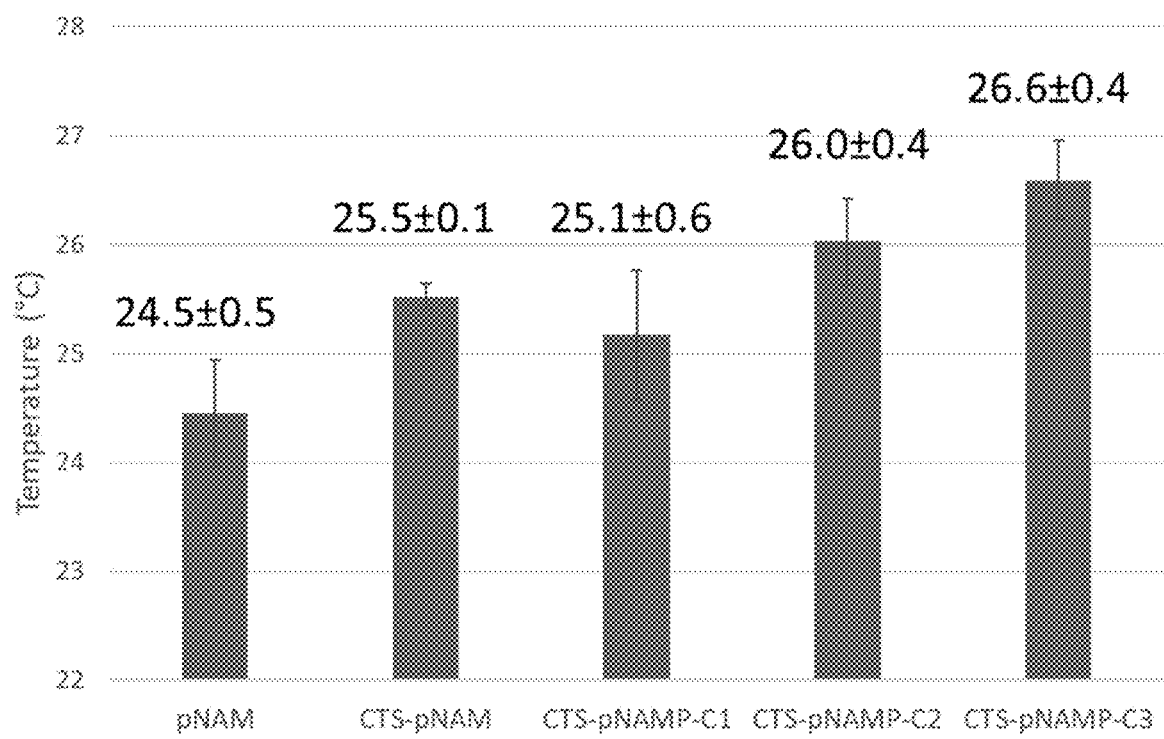

FIG. 19 shows the LCST of the exemplary pNAM and CTS-pNAM thermo-gels as well as the cysteamine modified thermo-gels CTS-pNAM-C1, CTS-pNAM-C2 and CTS-pNAM-C3, as determined by temperature ramps.

Figure 20:
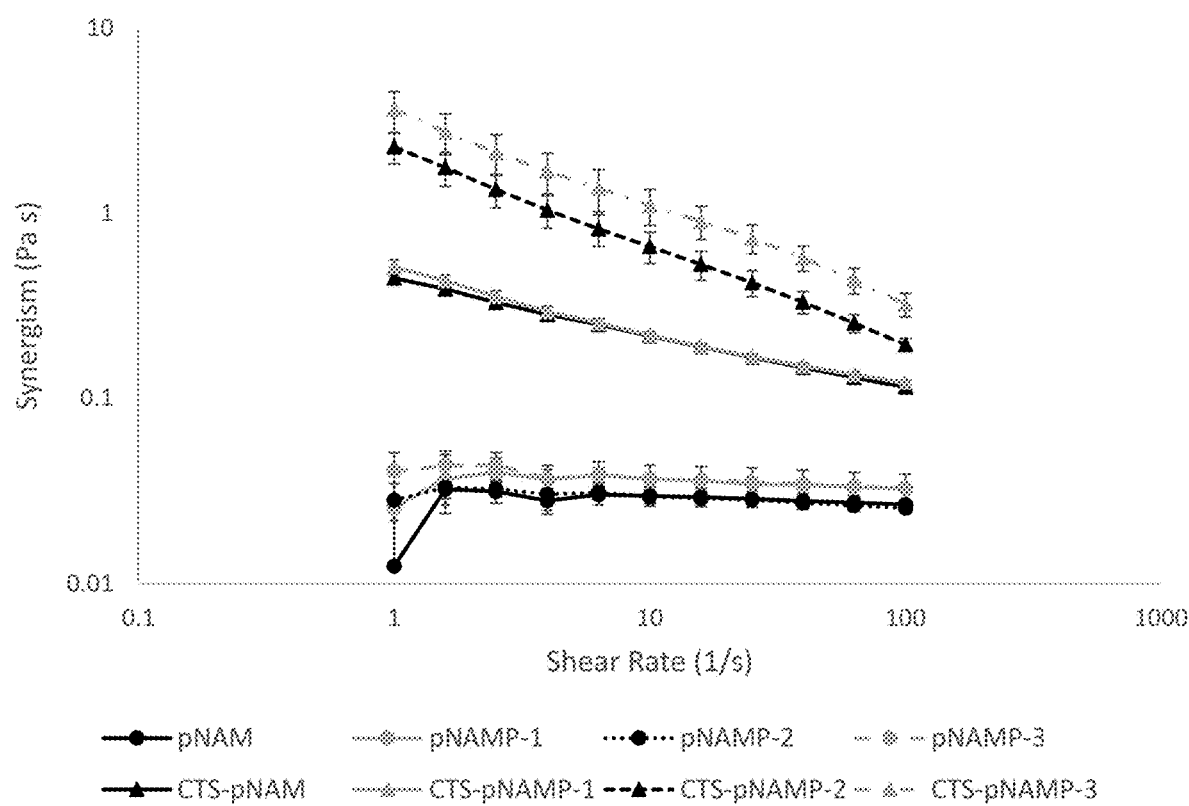

FIG. 20 shows the muco-adhesive properties of the exemplary thermo-gels produced in Example 2 determined by rheological synergism.

Figure 21:
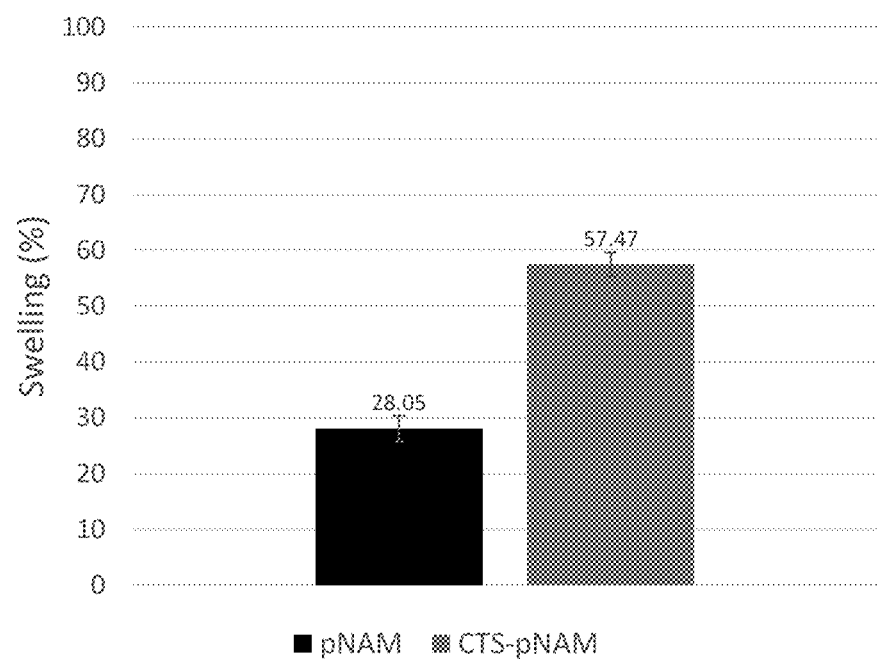

FIG. 21 shows the swelling properties of exemplary pNAM and CTS-pNAM. The swelling properties were statistically different ($p<0.05$)

Figure 22:
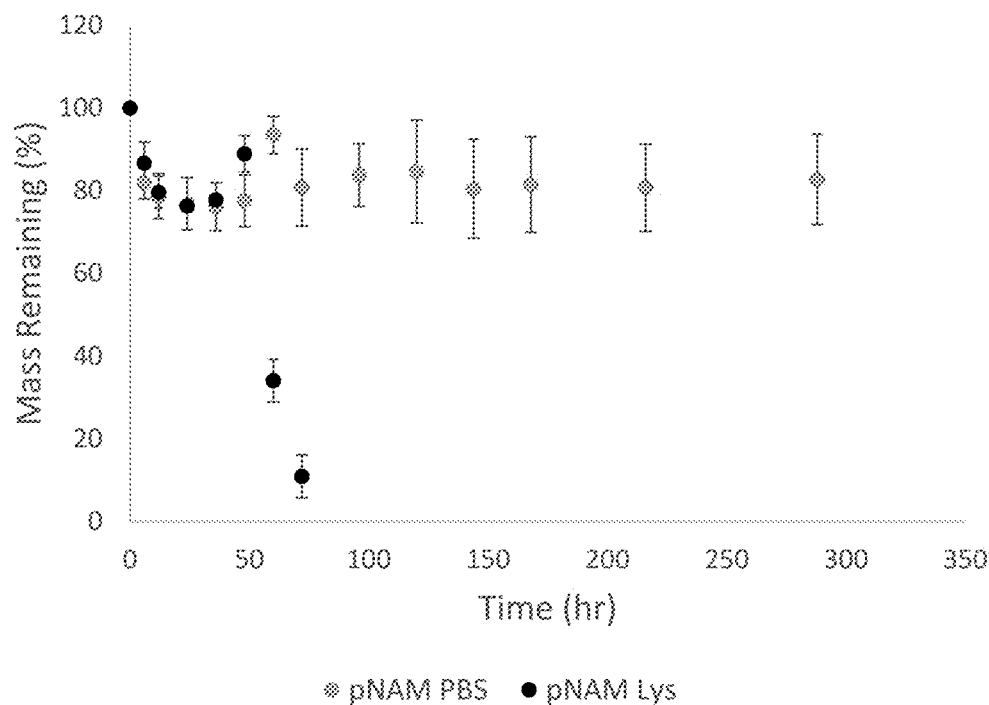
Figure 22:
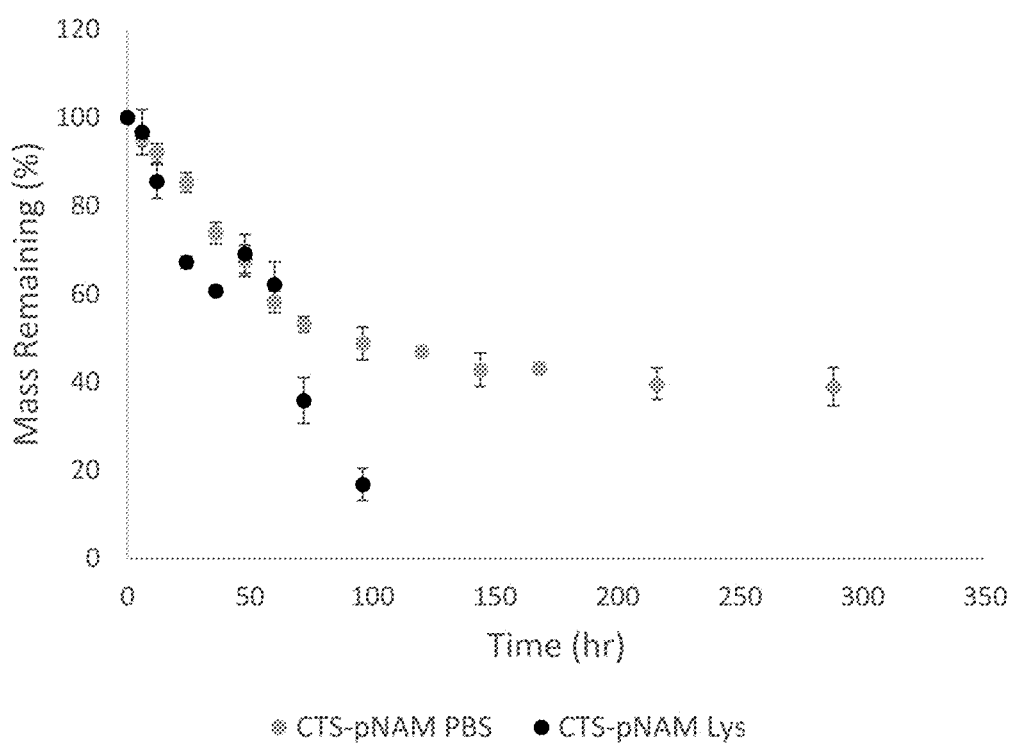

FIG. 22 shows degradation with PBS and PBS containing the physiological concentration of lysozyme for exemplary a) pNAM and b) CTS-pNAM.

Figure 23:
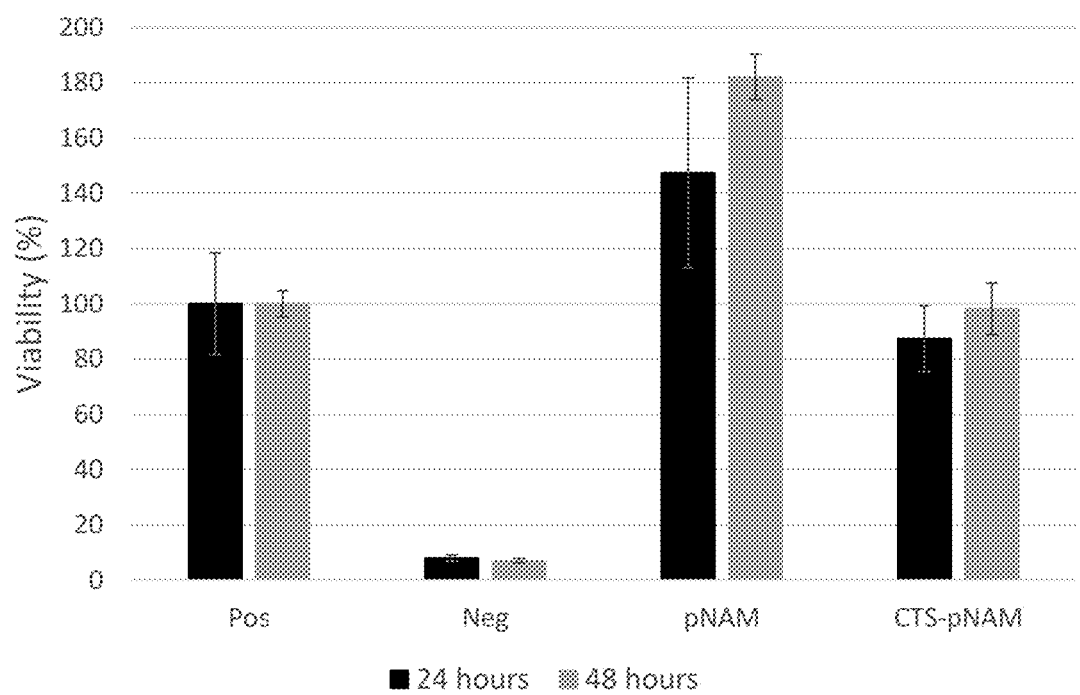

FIG. 23 shows the results of the MTT assay of exemplary pNAM and CTS-pNAM treated human corneal epithelial cells at 24 and 48 hours. Statistically higher ($p<0.05$) viability with pNAM at 24 hours compared to untreated cells. No statistically difference ($p>0.05$) between untreated cells and cells treated with CTS-pNAM.

Figure 24:
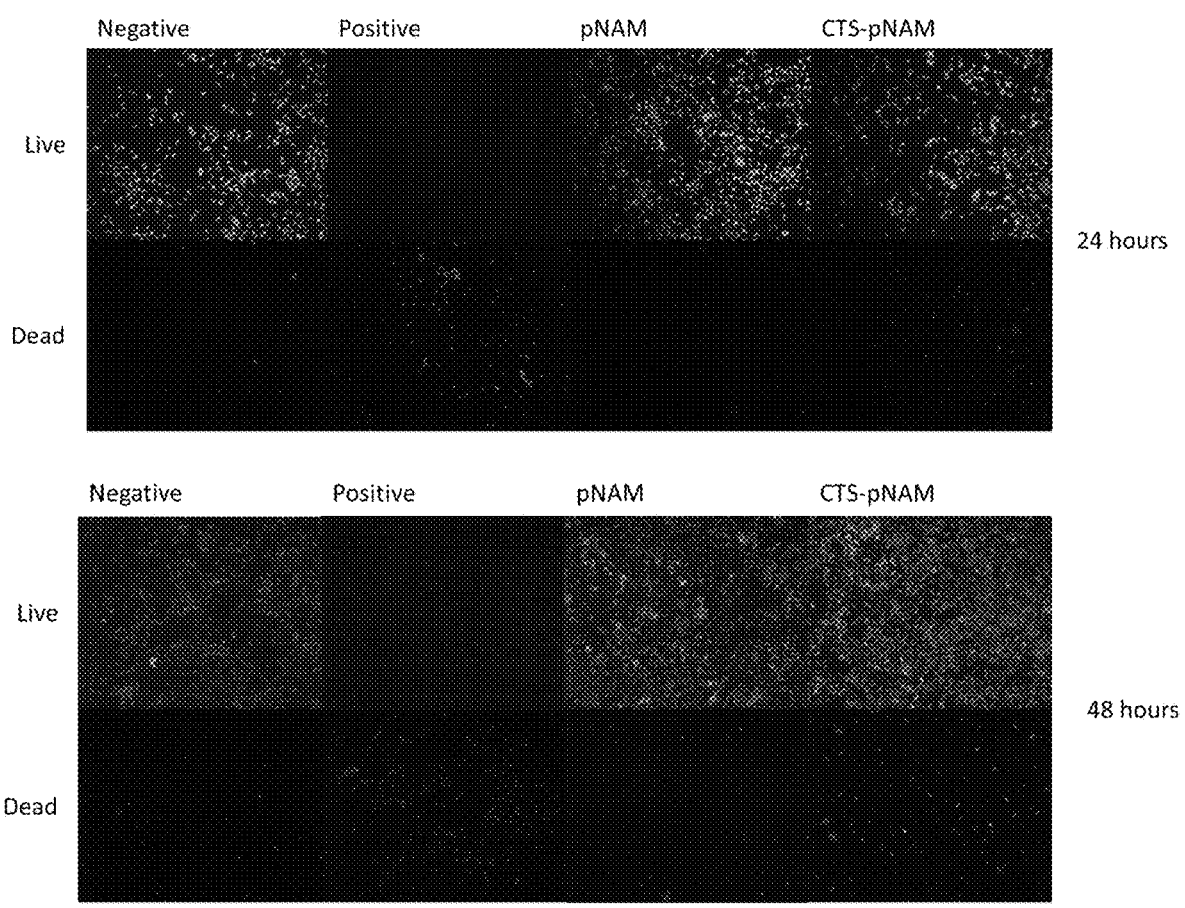

FIG. 24 shows live/dead staining of human corneal epithelial cells treated with exemplary pNAM and CTS-pNAM thermo-gels after 24 and 48 hours. There was no observable difference in cell morphology or death.

Figure 25:
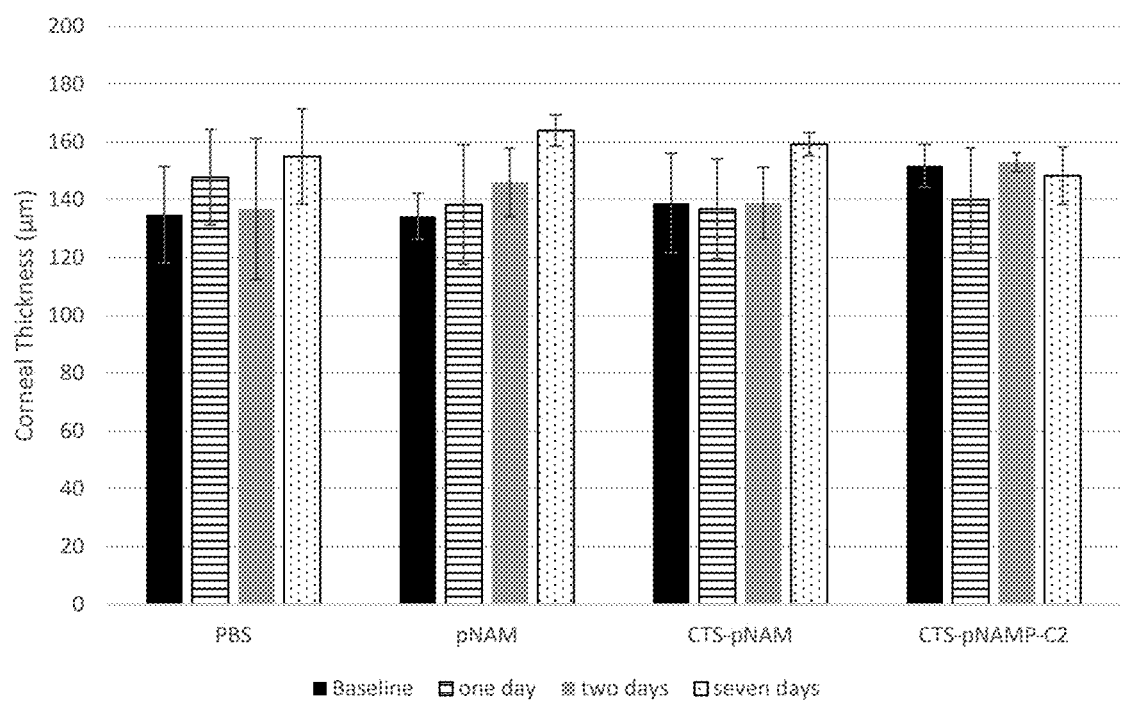

FIG. 25 shows the OCT measurement of Rat corneal thickness following daily treatment with PBS and exemplary pNAM, CTS-pNAM and CTS-pNAMP-C2. No statistical difference in corneal thickness except for pNAM and CTS-pNAM after 7 days of treatment.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

The term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The term "consisting" and its derivatives, as used herein, are intended to be closed terms that specify the presence of the stated features, elements, components, groups, integers, and/or steps, but exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise.

In embodiments comprising an "additional" or "second" component, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "thermo-gel" of the application as used herein refers to a any thermo-gel comprising a polymer and chitosan as described herein, wherein the polymer comprises monomers of N-isopropylacrylamide (NIPAAm), acrylic acid (AA) and at least one hydrophobic monomer.

A "polymer comprising a monomer" as used herein refers to polymers in which the recited monomers have been reacted in a polymerization reaction so that the various monomers, or monomeric units, are covalently bonded together.

The term lower critical solution temperature (LCST) as used herein refers to the temperature in which the value of the storage modulus (G') increases above the loss modulus (G") indicating gel formation.

The term "treating" or "treatment" as used herein and as is well understood in the art, means an approach for obtaining beneficial or desired results, including clinical results. Beneficial or desired clinical results include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease and remission (whether partial or total), whether detectable or undetectable. "Treating" and "treatment" can also mean prolonging survival as compared to expected survival if not receiving treatment. "Treating" and "treatment" as used herein also include prophylactic treatment. Treatment methods comprise administering to a subject a therapeutically effective amount of one or more of the thermo-gels of the application and optionally consist of a single administration, or alliteratively comprise a series of administrations.

As used herein, the term "effective amount" or "therapeutically effective amount" means an amount of one or more therapeutic agents that is effective, at dosages and for periods of time necessary to achieve the desired result.

The term "administered" as used herein means administration of a therapeutically effective amount of one or more therapeutic agents or thermo-gels of the application to a cell, tissue, organ or subject.

The term "therapeutic agent" as used herein refers to any drug or active agent that has a pharmacological effect when administered to a subject.

The term "subject" as used herein includes all members of the animal kingdom including mammals, and suitably refers to humans. Thus the methods of the present application are applicable to both human therapy and veterinary applications.

I. Thermo-Gels of the Application

The association of chitosan to the carboxylic acids of pNAM, by either covalent conjugation or ionic interaction, raises polymer LCST. In the present application, a base polymer is prepared having a lower LCST which maximizes the amount of chitosan which can be incorporated.

Therefore, the present application includes a thermo-gel comprising:
a) a polymer (pNAX), comprised of monomers of N (N-isopropylacrylamide (NIPAAm)), A (acrylic acid (AA)) and X (a hydrophobic monomer); and
b) chitosan,
wherein the chitosan is covalently or ionically bonded to the polymer.

In some embodiments, the hydrophobic monomer (X) in the thermo-gel is selected from, but not limited to, methyl acrylate, methyl methacrylate, ethyl acrylate, ethyl methacrylate, butyl acrylate, butyl methacrylate, isobutyl acrylate, isobutyl methacrylate, 2-ethylhexyl acrylate, tert-butyl acrylate, tert-butyl methacrylate, cyclohexyl methacrylate, phenyl methacrylate, 3-[tris(trimethylsiloxy)silyl]propyl methacrylate, and pyridyl disulfide ethyl methacrylate and derivatives thereof, including but not limited to 2-(pyridin-2-yldisulfaneyl)ethyl acrylate, N-(2-(pyridin-2-yldisulfaneyl)ethyl)methacrylamide, 3-(pyridin-2-yldisulfaneyl)propyl methacrylate, 2-(pyridin-2-yldisulfaneyl)ethyl methacrylate, 2-(2-pyridin-2-yldisulfanyl)ethyl-2-(methacrylamido)acetate and N-(3-(3-(pyridin-2-yldisulfanyl)propanamido)propyl)methacrylamide.

In some embodiments, the polymer further comprises one or more additional monomers. In some embodiments, the one or more additional monomers are hydrophobic monomers. In some embodiments, the one or more hydrophobic monomers are independently selected from, but are not limited to, methyl acrylate, methyl methacrylate, ethyl acrylate, ethyl methacrylate, butyl acrylate, butyl methacrylate, isobutyl acrylate, isobutyl methacrylate, 2-ethylhexyl acrylate, tert-butyl acrylate, tert-butyl methacrylate, cyclohexyl methacrylate, phenyl methacrylate, 3-[tris(trimethylsiloxy) silyl]propyl methacrylate, and pyridyl disulfide ethyl methacrylate and derivatives thereof, including but not limited to 2-(pyridin-2-yldisulfaneyl)ethyl acrylate, N-(2-(pyridin-2-yldisulfaneyl)ethyl)methacrylamide, 3-(pyridin-2-yldisulfaneyl)propyl methacrylate, 2-(pyridin-2-yldisulfaneyl)ethyl methacrylate, 2-(2-pyridin-2-yldisulfanyl)ethyl-2-(methacrylamido)acetate and N-(3-(3-(pyridin-2-yldisulfanyl)propanamido)propyl)methacrylamide.

In some embodiments, the one or more additional monomers are monomers comprising a disulfide moiety. In some embodiments, the one or more additional monomers comprising a disulfide moiety are selected from 2-((2-aminoethyl)disulfaneyl)ethyl methacrylate, 2-((2-aminoethyl)disulfaneyl)ethyl acrylate, N-(2-((2-aminoethyl)disulfaneyl)ethyl)acrylamide, and N-(2-((2-aminoethyl)disulfaneyl)ethyl)methacrylamide.

In some embodiments, when the polymer comprises one hydrophobic monomer X, the polymer comprises 60-98.5 mol % NIPAAm, 1-10 mol % AA and 0.5-30 mol % of the hydrophobic monomer X. In some embodiments, when the polymer comprises one hydrophobic monomer X, the polymer comprises about 88 mol % NIPAAm, about 2 mol % AA and about 10 mol % of the hydrophobic monomer.

In some embodiments, when the polymer comprises one or more additional monomers, the polymer comprises 60-98.5 mol % NIPAAm, 1-10 mol % AA, 0.5-30 mol % of X and 0.5-30 mol % of the one or more additional monomers. In some embodiments, the polymer comprises two independently selected hydrophobic monomers, and the polymer comprises about 85 mol % to about 87 mol % NIPAAm, about 2 mol % AA, about 10 mol % of a first hydrophobic monomeric unit and about 1 mol % to about 3 mol % of a second monomeric unit.

In some embodiments, at least one of the hydrophobic monomers comprises a disulfide moiety. In some embodiments, the hydrophobic monomers comprising a disulfide moiety are selected from 2-(pyridin-2-yldisulfaneyl)ethyl acrylate, N-(2-(pyridin-2-yldisulfaneyl)ethyl)methacrylamide, 3-(pyridin-2-yldisulfaneyl)propyl methacrylate, 2-(pyridin-2-yldisulfaneyl)ethyl methacrylate, 2-(2-pyridin-2-yldisulfanyl)ethyl-2-(methacrylamido)acetate and N-(3-(3-(pyridin-2-yldisulfanyl)propanamido)propyl)methacrylamide. In some embodiments, the hydrophobic monomer comprising a disulfide moiety is 2-(pyridin-2-yldisulfaneyl)ethyl acrylate. In some embodiments, the presence of a disulfide moiety improves the mucin binding of the thermo-gel.

In some embodiments, the hydrophobic monomer comprising a disulfide moiety comprises a therapeutic leaving group linked to a polymerizable moiety via the disulfide bond. In this embodiment cleavage of the disulfide bond by muco-adhesion results in release of the therapeutic group in vivo. In some embodiments, the therapeutic leaving group is selected from cysteamine, n-acetylcysteine, mercaptoethanol, cysteine and the thiolated adhesion peptide arginine-glycine-aspartic acid-cysteine. In some embodiments the therapeutic leaving group is cysteamine. In some embodiments, the therapeutic leaving group is cleaved during muco-adhesion.

In some embodiments, the polymer is a terpolymer comprising NIPAAm, AA and methymethacrylate (MMA). In some embodiments the terpolymer comprises 60-98.5 mol % NIPAAm, 1-10 mol % AA and 0.5-30 mol % of MMA. In some embodiments the terpolymer comprises about 88 mol % NIPAAm, about 2 mol % AA and about 10 mol % of MMA.

In some embodiments, the polymer is a tetrapolymer comprising NIPAAm, AA, MMA and a monomer comprising a disulfide moiety. In some embodiments the tetrapolymer comprises 60-98.5 mol % NIPAAm, 1-10 mol % AA, 0.5-30 mol % of MMA and 1-10 mol % of the monomer comprising a disulfide moiety. In some embodiments the tetrapolymer comprises about 85 mol % to about 87 mol % NIPAAm, about 2 mol % AA, about 10 mol % of a first hydrophobic monomeric unit and about 1 mol % to about 3 mol % of the monomer comprising a disulfide moiety. In some embodiments, the monomer comprising a disulfide moiety is a hydrophobic monomer comprising a disulfide moiety and is selected from 2-(pyridin-2-yldisulfaneyl)ethyl acrylate, N-(2-(pyridin-2-yldisulfaneyl)ethyl)methacrylamide, 3-(pyridin-2-yldisulfaneyl)propyl methacrylate, 2-(pyridin-2-yldisulfaneyl)ethyl methacrylate, 2-(2-pyridin-2-yldisulfanyl)ethyl-2-(methacrylamido)acetate and N-(3-(3-(pyridin-2-yldisulfanyl)propanamido)propyl) methacrylamide. In some embodiments, the hydrophobic monomer comprising a disulfide moiety is 2-(pyridin-2-yldisulfaneyl)ethyl acrylate. In some embodiments, the one or more additional monomers are monomers comprising a disulfide moiety. In some embodiments, the monomer comprising a disulfide moiety is selected from 2-((2-aminoethyl)disulfaneyl)ethyl methacrylate, 2-((2-aminoethyl)disulfaneyl)ethyl acrylate, N-(2-((2-aminoethyl)disulfaneyl)ethyl)acrylamide, and N-(2-((2-aminoethyl)disulfaneyl)ethyl)methacrylamide.

In some embodiments, the uncrosslinked polymer has a molecular weight of about 1,000 g/mol to about 1,000,000 g/mol, or about 55,000 g/mol to about 66000 g/mol or about 61,500±5300 g/mol.

In some embodiments the polymer is a polymer prepared by polymerization of N (N-isopropylacrylamide (NIPAAm)), A (acrylic acid (AA)) and at least one X (a hydrophobic monomer). In some embodiments, the polymer is prepared by free radical polymerization. In some embodiments, the molar ratio of N:A:X in the reaction feed is about 80-88:2-5:10-15 mol %. In some embodiments, when the polymer includes a monomer comprising a disulfide moiety, the molar ratio of N:A:X:disulfide monomer in the reaction feed is about 80-88:2-5:10-15:1-5. In some embodiments the polymerization reaction is performed at about 50° C. to about 90° C., or at about 70° C., for about 12 hours to about 36 hours, or about 24 hours.

In some embodiments, the chitosan is covalently conjugated to the polymer. In some embodiments the chitosan is covalently conjugated to the polymer using a coupling reagent. In some embodiments, the coupling reagent is selected from 1-ethyl-3-(3-dimethyl aminopropyl)-carbodiimide (EDC), O-(benzotriazol-1-yl)-N,N,N',N'-tetramethyluronium hexafluorophosphate (HBTU), bis(2-oxo-3-oxazolidinyl)phosphinic chloride (BOP-Cl), 2-chloro-4,6-dimethoxy-1,3,5-triazine (CDMT), (chloromethylene) dimethyliminium chloride (Vilsmeier reagent), carbonyl diimidazole (CDI), propylphosphonic anhydride, diethyl chlorophosphite and dicyclohexylcarbodiimide (DCC). In some embodiments, the coupling reagent is 1-ethyl-3-(3-dimethyl aminopropyl)-carbodiimide (EDC).

In some embodiments, the chitosan is conjugated to the polymer by ionic bonds.

With the incorporation of AA directly into the polymer backbone, the base polymer is both a pH and thermo-sensitive polymer. When dissolved in solution at 20 wt/v and X is methacrylate, the polymer has a pH of 4.37 which is reflective of the pKa value of acrylic acid. In some embodiments, the pH of the thermo-gel is when dissolved in solution is 6.5 or below.

In some embodiments, the lower critical solution temperature (LCST) of the thermo-gel is slightly lower than physiological temperature, ideally below about 34-37° C., or between about 25° C. and about 32° C.

In some embodiments, the initial LCST of the thermo-gel is lowered by the addition of the hydrophobic monomeric unit(s), allowing for more chitosan to be incorporated and yielding a crosslinked system with an ideal LCST for anterior ocular drug delivery. In some embodiments, controlling the amount of chitosan crosslinked into the system allows for control of the mechanical properties of the thermo gel which dictate the degradation and drug release profiles.

In some embodiments, acrylic acid is incorporated throughout the polymer, allowing for increased number of crosslinks of the polymer with chitosan. The majority of studies which graft chitosan on pNIPAAm chains, particularly in the ophthalmic space, utilize a synthetic scheme in which pNIPAAm chains are end-capped with a carboxylic acid rather than incorporating carboxylic acid throughout the polymer backbone. The end-capped pNIPAAm polymer chains are then covalently grafted to chitosan by use of a carbodiimide. By synthesizing a polymer, wherein the carboxylic acid is incorporated throughout the polymer backbone, there will be an intrinsic difference in both base polymer properties and the hydrogels properties, once crosslinked with chitosan. By incorporating carboxylic acid moieties along the polymer, both chitosan and the polymer can be conjugated anywhere along their polymer chains, limited only by carbodiimide concentration, amine/carboxylic acid concentration and steric hinderance. This contrasts with end-capped pNIPAAm which can only be conjugated at those terminal moieties along the backbone of chitosan. Therefore, in some embodiments, the thermo-gels of the present application are stiffer due to the higher degree of possible conjugation between the two polymer chains compared to hydrogels produced from end-capped pNIPAAm. Unlike hydrogels based on end-capped pNIPAAm, the resulting thermo-gels of the present application will have a pH relationship based on the concentration of unreacted carboxylic acids on the polymer backbone.

The degradation of removal of the thermo-gel from the inferior fornix of the eye within a few days, will be affected by the properties of chitosan. In some embodiments, chitosan having a low deacetylation (DDA) and a low molecular weight promotes degradation by lysozyme.

In some embodiments, the thermo-gel comprises up to about 5 wt % chitosan with the chitosan having about 50 to about 80 degree of deacetylation (DDA), and a molecular weight of about 10 kDa to about 300 kDa or about 10 kDa to about 100 kDa. In some embodiments, the thermo-gel comprises about 1 wt % to about 5 wt % of the chitosan.

In some embodiments, the thermo-gel is used for anterior ocular drug delivery, and is applied to the inferior fornix or cul-de-sac of the eye. Therefore, in some embodiments, the thermogel further comprises one or more therapeutic agents. In some embodiments, the one or more therapeutic agents are selected from drugs useful to treat ophthalmic conditions, including but not limited to drugs for anti-allergy (decongestant, antihistamine, mast cell stabilizers, non-steroidal anti-inflammatory drug (NSAID) and corticosteroids); glaucoma (parasympathomimetic, sympathomimetic, prostaglandin analogs, beta blockers, alpha agonists ($\alpha$1-blockers and $\alpha$2-adrenergic agonists), carbonic anhydrase inhibitors, rho kinase inhibitors); dry eye (lubricating agents and electrolytes); bacterial conjunctivitis (aminoglycosides, fluoroquinolones, polymyxin B combination, macrolides, sulfonamides, chloramphenicol, vancomycin and tetracyclines); pain relievers (NSAIDs, corticosteroids and local anesthetics); uveitis (corticosteroids, antimetabolites, T-cell inhibitors, alkylating agents and monoclonal antibodies) and biologic compounds (proteins, cells and peptides), and combinations thereof. In some embodiments, the proteins are growth factors and/or antibodies In some embodiments, the one or more therapeutic agents are present in the hydrogel in therapeutically effective amounts, which will vary depending on identity of the agent but can be determined by a person skilled in the art. For example, the therapeutically effective amounts of the one or more therapeutic agents varies depending on many factors such as the pharmacodynamic properties of the agent, the mode of administration, the age, health and weight of the recipient, the nature and extent of the symptoms, the frequency of the treatment and the type of concurrent treatment, if any and the clearance rate of the agent in the subject to be treated. One of skill in the art can determine the appropriate therapeutically effective amount based on the above factors.

III. Methods of the Application

In some embodiments, the thermo-gel is used to treat ophthalmic conditions including, but not limited to, cystinosis, corneal healing, glaucoma, ophthalmic pain relief, glaucoma, allergic conjunctivitis, dry eye, infection, uveitis and/or post-surgical applications to increase healing.

Therefore in some embodiments, the present application includes a method of treating one or more ophthalmic conditions comprising administering an effective amount of a thermo-gel of the application to a subject in need thereof.

Also included is a use of a thermo-gel of the application to treat one or more ophthalmic conditions and a use of a thermo-gel of the application to prepare a medicament to treat one or more ophthalmic conditions.

In some embodiments, the thermo-gel of the application comprises a therapeutically effective amount of one or more therapeutic agents.

In some embodiments, administration of the thermo-gel is to the inferior fornix or cul-de-sac of the eye for anterior ocular drug delivery.

In some embodiments, the one or more ophthalmic conditions is cystinosis. Cystinosis, is a multisystem recessive genetic disorder characterized by a buildup of crystals consisting of the amino acid cysteine in various tissues and organs throughout the body. The intracellular accumulation of cysteine and subsequent crystal formation is caused by the defective action of the lysosomal transmembrane protein cystinosin. In some embodiments, for the treatment of cystinosis, the thermo-gel of the application comprises a polymer having one or more monomers comprising a disulfide moiety. Therefore in some embodiments, the present application includes a method of treating cystinosis comprising administering an effective amount of a thermo-gel of the application to a subject in need thereof. Also included is a use of a thermo-gel of the application to treat cystinosis and a use of a thermo-gel of the application to prepare a medicament to treat cystinosis. It is an embodiment, that the thermo-gel used to treat cystinosis comprises a monomer comprising a disulfide moiety.

The present application also includes a method of improving mucoadhesive properties of a thermo-gel comprising incorporating one or more monomers comprising a disulfide moiety into a polymer comprised in the thermo-gel.

In further embodiments, the thermo-gels of the present application are used for additional applications including but not limited to contact lens materials, or transdermal drug delivery.

Therefore the present application includes a contact lens comprising one or more thermo-gels of the application.

Also included is a method for transdermal delivery of one or more therapeutic agents comprising administering a thermo-gel of the application to the skin of a subject, wherein the thermo-gel comprises the one or more therapeutic agents. Further the application includes a use of a thermo-gel of the application for transdermal delivery of one or more therapeutic agents.

The following non-limiting examples are illustrative of the present application:

EXAMPLES

Example 1: pNAM Polymer+10-50 kDa Chitosan Thermo-Gel

Materials

Chitosan (MW=10-50 kDa, DDA=70%) was purchased from Heppe Medical Chitosan (Halle, Saxony-Anhalt, Germany) and used as received. N-isopropylacrylamide (NIPAAm; 97%) was purchased from Sigma-Aldrich (Oakville, Ontario, Canada) and purified by recrystallization from toluene with n-hexane. Acrylic acid (AA; 99%) was purchased from Sigma-Aldrich and purified by passing through a packed column containing Sigma-Aldrich inhibitor remover to remove the inhibitor 4-methoxyphenol. Methyl methacrylate (MMA; 99%), benzoyl peroxide (BPO; Luperox®, 98%), N-(3-dimethylaminopropyl)-N'-ethylcarbodiimide hydrochloride (EDC; BioXtra), and 2-(N-morpholino)ethanesulfonic acid (MES; free acid) were purchased from Sigma-Aldrich and used as received. 1,4-Dioxane, n-hexane, toluene, anhydrous diethyl ether and tetrahydrofuran (THF) were purchased from VWR (Radnor, Pennsylvania, USA) and used as received. Milli-Q grade deionized water was prepared using a Barnstead Diamond™ water purification system (Thermo Fischer Scientific, Waltham, Massachusetts, USA). 10× Phosphate buffered saline (PBS) was purchased from BioShop® (Burlington, Ontario, Canada) and diluted with deionized water to 1× (pH 7.4) for all experiments. All other compounds were purchased from Sigma Aldrich (Oakville, Ontario, Canada) unless otherwise specified.

Poly(n-isopropylacrylamide-co-Acrylic Acid-co-methyl methacrylate) (pNAM) Synthesis The free radical pNAM terpolymers were produced by methods similar to those previously reported [20-22]. The free radical synthetic pathway is visualized in FIG. 1a). 3.8 g (33.6 mmol) of recrystalized NIPAAm, 30 mg (0.4 mmol) uninhibited AA, 170 mg (1.7 mmol) of methyl methacrylate (MMA) and 18 mg of benzoyl peroxide (BPO) (0.1 mmol) were dissolved in a round bottom flask containing 40 mL of 1,4 Dioxane:Milli-Q Water (9:1 v/v) to produce 10% (wt/v) monomer solution. The molar feed ratio of NIPAAm:AA:MMA was 80:5:15. The solution was then degassed with nitrogen for 25 minutes. The purged flask was sealed and heated to 70° C. for 24 hours under constant stirring. Following the polymerization, the polymer solution was exposed to oxygen to terminate the reaction and cooled to room temperature. To remove any unreacted monomers, the polymeric solution was precipitated twice into 800 mL of anhydrous ethyl ether, separated by vacuum filtration over a fitted funnel and redissolved in tetrahydrofuran between precipitations. The resulting pNAM powder was placed in a vacuum oven to dry overnight before being dialyzed for 3 days against 4 L of deionized water using a Membra-Cel® 14 kDA MWCO cellulose membrane (Viskase®, Lombard, Illinois, USA). The pNAM sample was then finally lyophilized using a Labconco™ FreeZone 2.5 L benchtop freeze drier (Kansas City, Missouri, USA) and stored at −20° C.

The pNAM compositions were determined by $^1$H NMR using a Bruker© 600 MHz Spectrometer (Billerica, Massachusetts, USA), dissolving samples in deuterated dimethyl sulfoxide (DMSO-d$_6$). The MW of the pNAM were determined at room temperature by gel permeation chromatography (GPC) using a Polymer Laboratories PL-50 gel permeation chromatographer (Church Streton, Shropshire, UK) fitted with three Phenomenex Phenogel™ columns; pore sizes 100, 500 and 104 Å (Torrance, California, USA), samples were dissolved in 10 wt/v in dimethylformamide containing 5 mM lithium bromide. GPC calibrations were performed using linear polyethylene glycol standards provided by Polymer Laboratories. All samples were filtered through a 0.2 μm PTFE syringe filter prior to quantification.

Results and Discussion

Figure 2:
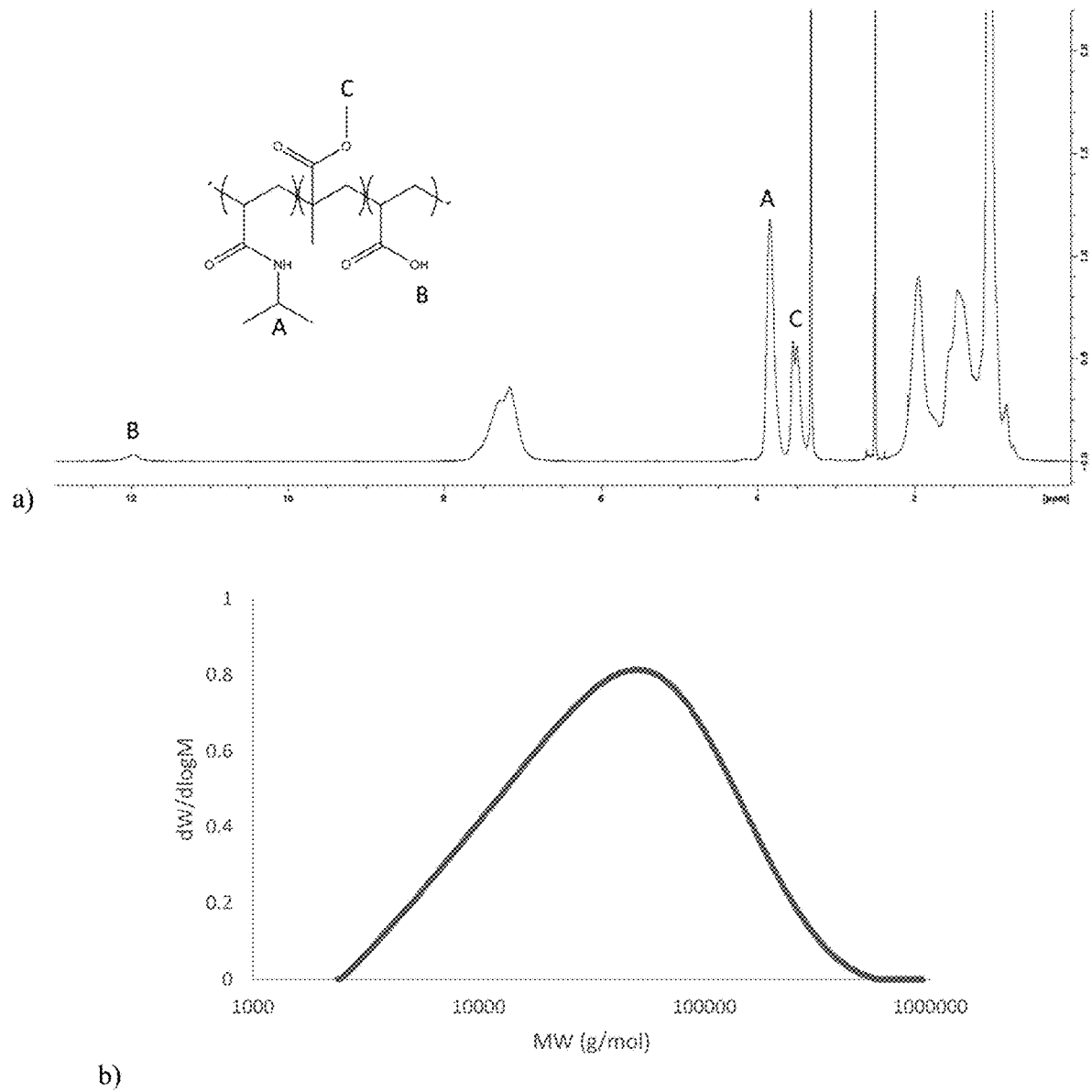
FIG. 2 shows a) $^1$H NMR analysis of pNAM (where M is the hydrophobic monomer methyl methacrylate) b) gel permeation chromatography (GPC) analysis of pNAM in an exemplary embodiment of the application.

The $^1$H NMR of pNAM is shown in FIG. 2a) and was used to determine the polymer's molar composition. The tertiary NH associated with the isopropyl tail of the NIPAAm units is present at 3.84 ppm (A), the hydroxyl group of AA at 12 ppm (B) and the methyl tail of MMA as a doublet at 3.54 and 3.50 ppm (C). The free radical polymerization of pNAM was found to be highly reproducible with a molar composition of 80.28±0.07, 4.10±0.06 and 15.61±0.08 of NIPAAm:AA:MMA across all batches. The GPC analysis of pNAM terpolymers is visualized in FIG. 2b). The average polymer molecular weight was determined to be 61,500±5300 g/mol across all pNAM batches.

Chitosan Crosslinked pNAM Networks

Figure 1:
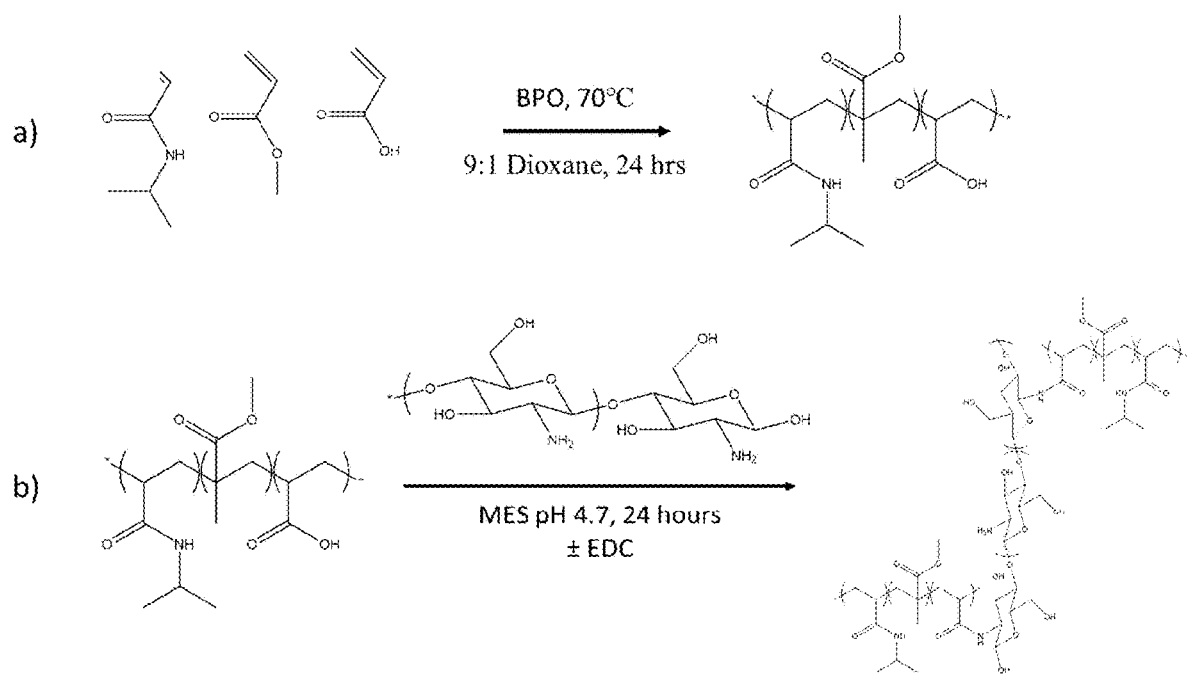
FIG. 1 shows a) free radical polymerization and b) covalent crosslinking of chitosan by EDC in exemplary embodiments of the application.

For the production of covalently crosslinked chitosan-graft-pNAM networks (CCN), similar methods were used as to those reported in literature, and visualized in FIG. 1b) [30, 49, 53]. Three CCN samples were produced containing 1, 3 and 5 wt % chitosan/pNAM. These samples are denoted as 1-CCN, 3-CCN and 5-CCN respectively. To produce 3-CCN; 90 mg chitosan was first dissolved in 10 mM MES buffer, adjusted to pH 4.7 using 0.1 N NaOH, at 1% (wt/v) and dissolved for 5 hours at 45° C. under constant stirring. Once dissolved the sample was filtered using a 0.2 nm syringe filter to remove any remaining aggregates. 3 g of pNAM sample was then added and allowed to dissolve before the dropwise addition of 862 mg (4.5 mmol) of EDC, which was dissolved in a minimal volume of MES buffer. The solution reacted for 24 hours at room temperature under constant stirring. The CCN samples were then dialyzed for three days against 4 L deionized water using Spectrum Labs 3.5 kD MWCO Spectra/Por regenerated cellulose dialysis membrane (VWR, Radnor, Pennsylvania, USA) before being lyophilized and stored at −20° C. For polyelectrolyte complexes of physically crosslinked chitosan to pNAM via ionic interactions, (PEC) the same procedure was used but without the addition of EDC.

The CCN and PEC polymer networks were characterized by a Fourier Transform Infrared (FTIR; Thermo scientific, Waltham, Massachusetts, USA) with a wavenumber range of 400 to 4000 cm$^{-1}$. The CCN and PEC network sizes were determined by aqueous GPC. The samples were dissolved to 5 wt/v in acetate buffer adjust to pH 4.7.

Results and Discussion

Figure 3:
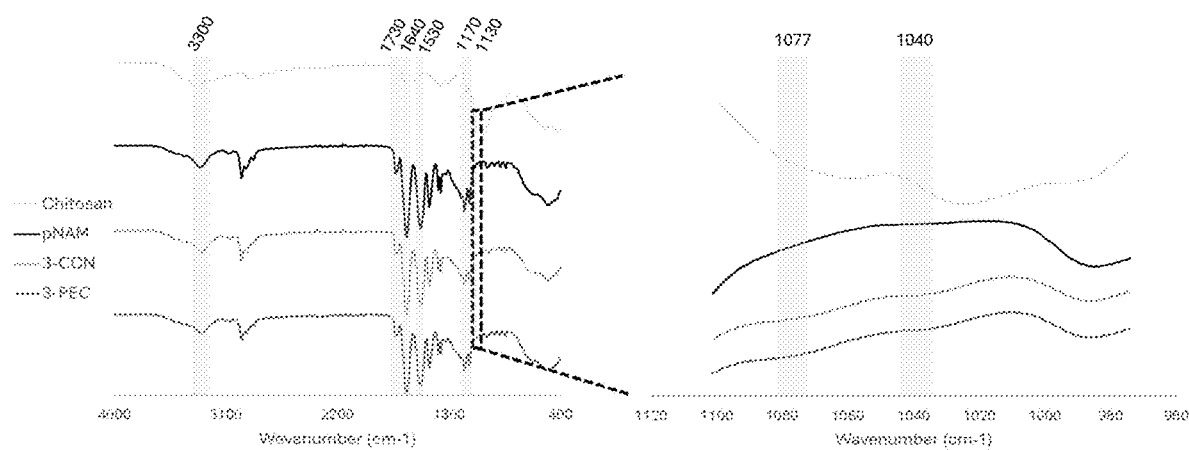
FIG. 3 shows FITR spectra of a) Chitosan, b) exemplary pNAM, c) exemplary 3-CCN and d) exemplary 3-PEC.

Hydrogel compositions were characterized by FTIR analysis with a wavenumber range of 400 to 4000 cm$^{-1}$. The FTIR spectra for chitosan, pNAM, 3-CCN and 3-PEC are shown in FIG. 3. The pNAM control spectra shares some peaks with chitosan because of the nature of the NIPAAm monomer: 3300 cm$^{-1}$ (NH stretch), 1640 cm$^{-1}$ (C=O stretch, amide I) and 1530 cm$^{-1}$ (NH bend, amide II). Incorporation of AA is seen at 1730 cm$^{-1}$ (carbonyl C=O stretch) and MMA at 1171 cm$^1$ (ester C—O) and 1130 cm$^{-1}$ (unconjugated ester —CO—O—CH$_3$ stretch) [54]. With the 3-CCN and 3-PEC samples, two new subtle peaks are observed at 1077 and 1039 cm$^{-1}$ which reflect the C—O—C and C—O stretches of the incorporated chitosan, respectively. However, the signal change is very small so additional characterization methods were used to confirm the incorporation of chitosan.

pH Relationships of Thermo-Gel Networks Dissolved in PBS

The pH measurements of the polymer networks dissolved at 20 wt/v in 1× PBS (pH 7.4) are shown in Table 1.

| Polymer Network | Batch pH |
| --- | --- |
| pNAM | 4.37 ± 0.2 |
| 1-CCN | 4.94 ± 0.1 |
| 3-CCN | 5.68 ± 0.1 |
| 3-PEC | 5.03 ± 0.0 |
| 5-CCN | 6.51 ± 0.1 |

The pNAM base polymer has a pH of 4.37 when dissolved in solution which is reflective of the pka of acrylic acid. With the addition of chitosan, the pH of solution increases regardless of covalent or ionic incorporation. The incorporation of chitosan by EDC conjugation results in a linear ($R^2$=0.995) increase of solution pH with the concentration of chitosan. The concentration of EDC used scaled directly with the concentration of chitosan added. With the greater amount of chitosan used, theoretically the higher the number of carboxylic acid units reacted from pNAM, as is sterically possible. The pH of 6.5 which is seen with 5-CCN theoretically represents the ceiling solution pH which can be achieved with chitosan before it is precipitated out of solution. Without the addition of EDC, the blending of chitosan and pNAM create polyelectrolyte complexes [55]. It can be seen from the samples 3-CCN and 3-PEC that the use of EDC conjugation results in a higher solution pH than the natural ionic interactions. This result was expected because EDC conjugation allows for the actual reaction of the carboxylic acid in pNAM and any unreacted groups are still available for ionic interactions.

For application to the anterior of the eye, a solution pH of approximately 6 is desired to avoid irritation. The pH of all polymer networks can be adjusted with base to a pH of approximately 6.5 before, experimentally, chitosan is precipitated out of solution.

Rheological Analysis

The rheological properties and LCST of polymer samples were determined by a Discovery HR-2 hybrid rheometer (Waters™, Newcastle, Delaware, USA), fitted with a 20 mm parallel aluminum Peltier plate. All samples were dissolved at a concentration of 20 wt/v in PBS for analysis. Strain sweeps were conducted at 37° C. to determine the range of the linear viscoelastic region (LVE) for all samples. Temperature ramps with a rate of 1° C./min, ranging from 15–45° C., were used to determine the LCST of polymer samples [15, 56]. The LCST is the temperature in which the storage modulus (G') increases above the loss modulus (G") indicating that the sample is a gel because it is behaving as a viscoelastic solid [57, 58]. Frequency sweeps were conducted at 37° C. to determine gel stiffness and compare the effect of increasing chitosan crosslinking and the effect of grafting chitosan by either covalent conjugation or physical ionic interactions [57].

Results and Discussion

Figure 4:
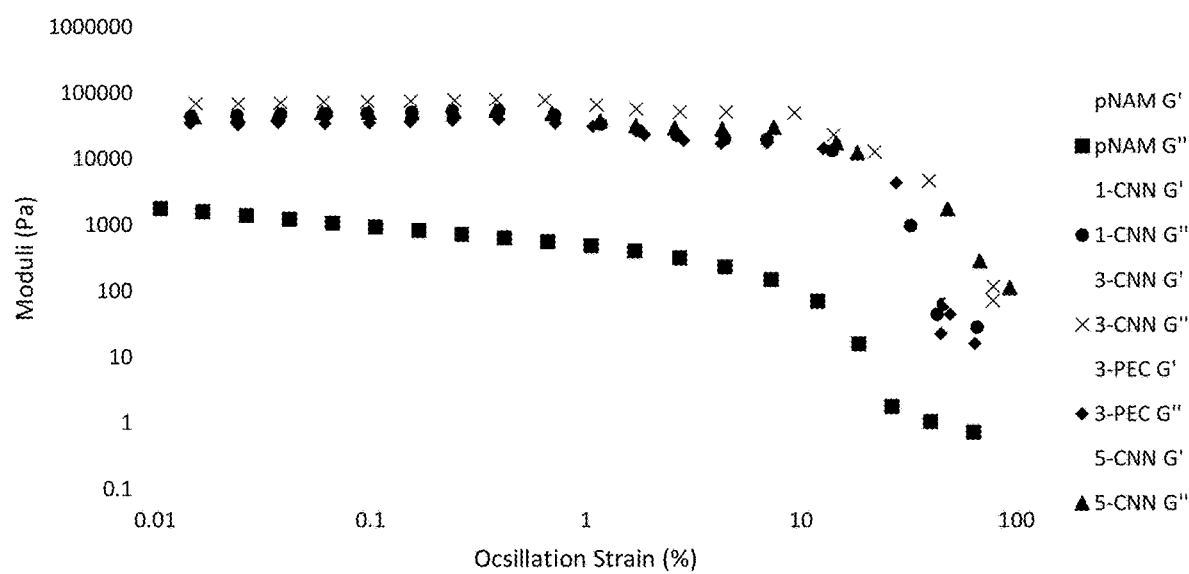
FIG. 4 shows stress strain analysis of exemplary pNAM, 1-CCN, 3-CCN, 3-PEC and 5-CCN polymer networks.

The strain sweeps of control pNAM, all CCN and 3-PEC samples are visualized in FIG. 4. It was determined that all hydrogel samples failed after an applied oscillation strain of greater than 10%. Therefore, for subsequent rheological experiments, an oscillation strain of 0.1% was used as it was well within the linear viscoelastic region of all the samples.

Figure 5:
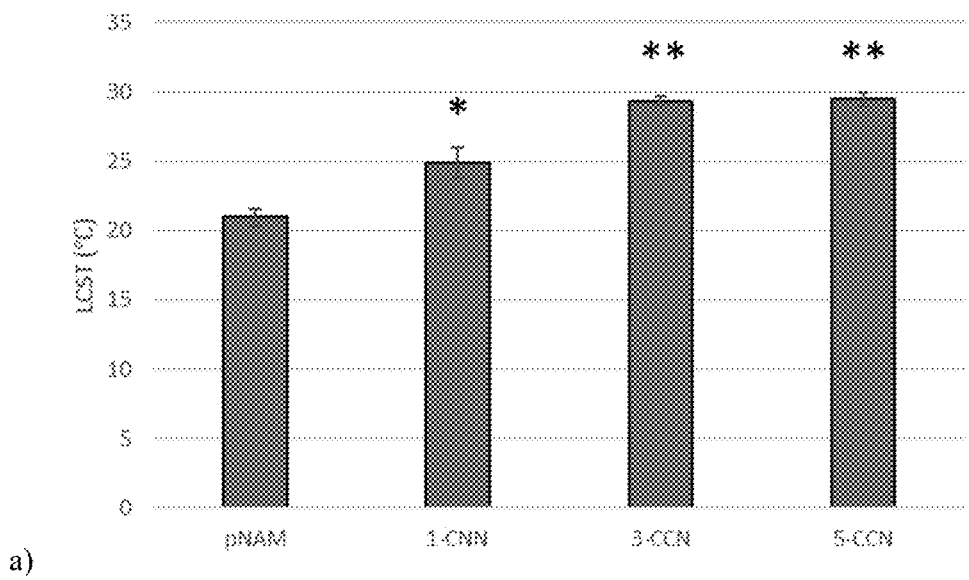
FIG. 5 shows LCST determination of a) covalently crosslinked networks of varying chitosan concentration and b) covalent Vs physical ionic incorporation of chitosan in an exemplary embodiment of the application.
Figure 5:
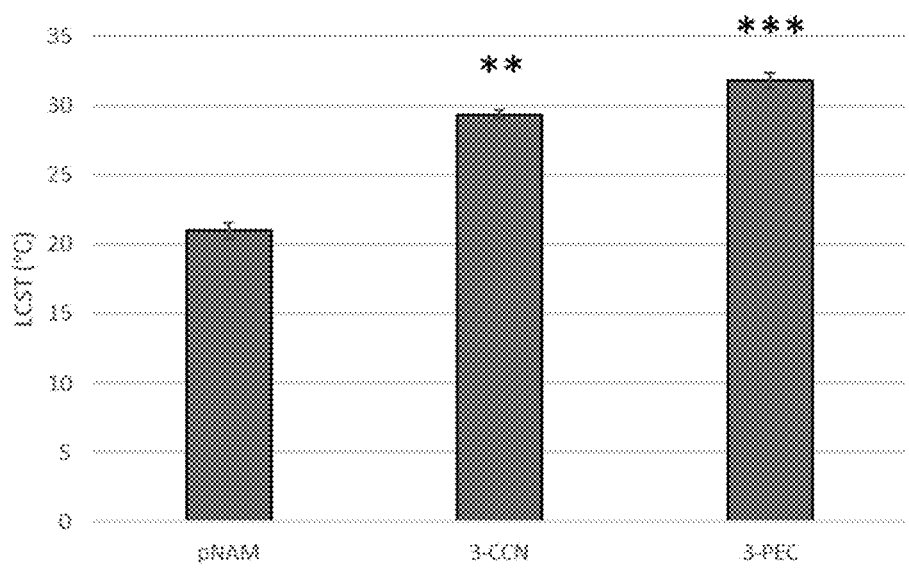

Initially, the LCST of base pNAM and covalently cross-linked networks containing 1, 3 and 5 wt % chitosan were tested, the results of which are shown in FIG. 5a). The base pNAM polymer had an LCST of 21.0° C., notably lower than the volume phase transition temperature of 27° C. reported by Okudan and Altay determined by gravimetric analysis for pNAM of the same molar composition [59]. It can be seen from FIG. 5a) that the LCST increases directly with the amount of covalently conjugated chitosan, as was expected. By reacting a higher number of the primary amines, and neutralizing those remaining by ionic interactions, chitosan becomes a predominantly hydrophilic cross-linker and therefore raises the systems LCST. The LCST of the hydrogels are a function of solution concentration, degree of grafting and chitosan properties. Luo et al., demonstrated an increase in LCST corresponding to an increase of the DDA of chitosan grafted with end-capped pNIPAAM [11]. For application to the inferior fornix of the eye, the thermo-gel is optimally able to withstand slightly colder temperatures, as low as 34° C., up to 37° C. [30]. From the LCST data, all the produced thermo-gels had an LCST below the cut off requirement of 34° C. Particularly, 3-CCN had an LCST which was greater than room temperature but significantly below the temperature of the anterior of eye.

The LCST comparison between covalently crosslinked networks and polyelectrolyte complexes of chitosan and pNAM is visualized in FIG. 5b). Both 3-CCN and 3-PEC have a higher LCST than the base pNAM polymer. 3-PEC has a slightly lower LCST when compared to 3-CCN as the blended chitosan is not as hydrophilic compared to when it is covalently grafted. Interestingly, 3-PEC has an LCST which is between 1-CCN and 5-CCN demonstrating that the concentration of chitosan in the hydrogel system has a greater impact than does the way in which it is incorporated.

Figure 6:
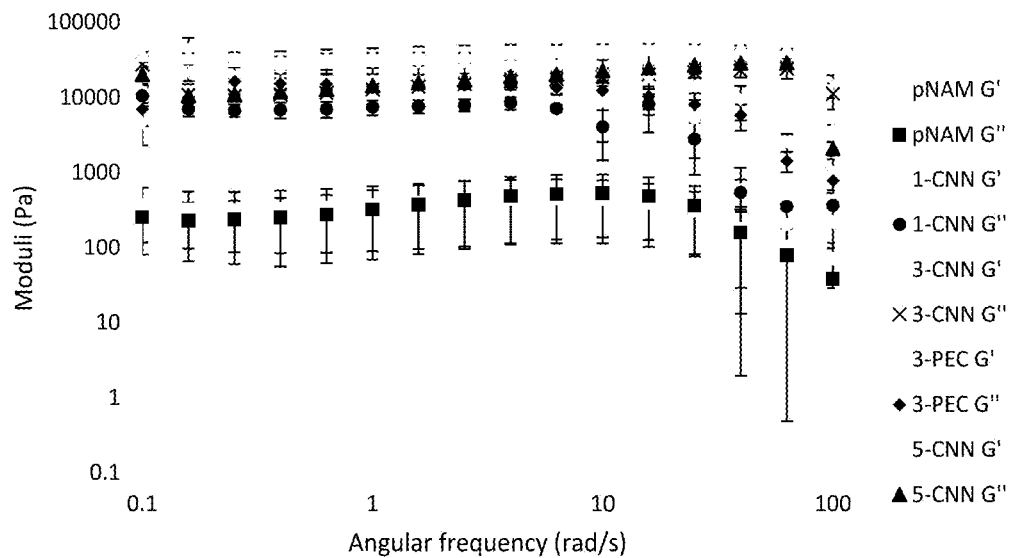
FIG. 6 shows a) exemplary thermo-gel frequency sweeps and b) exemplary thermo-gel moduli comparison at 1 rad/s.
Figure 6:
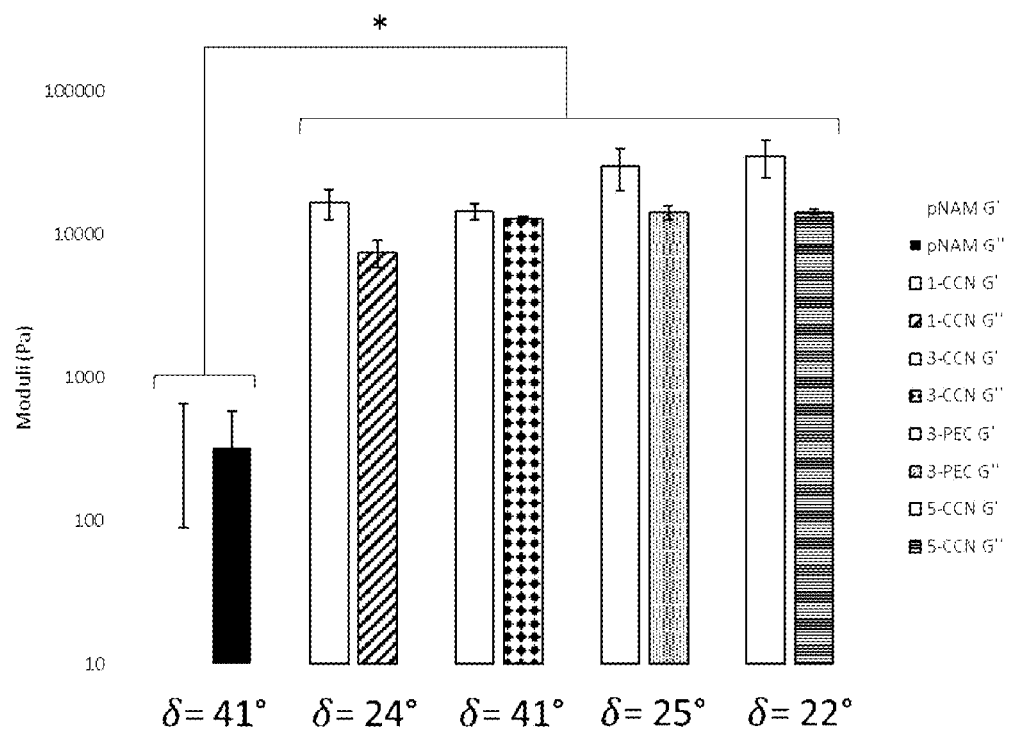

Frequency sweeps were used to determine the effect of chitosan concentration and incorporation, either by covalent conjugation or physical ionic interactions. The frequency sweeps of pNAM, all CCN and 3-PEC samples are visualized in FIG. 6a). FIG. 6b) shows the relationship between G' and G" at a constant angular frequency of 1 rad/s. Examining the frequency sweep at a lower set angular frequency, such as 1 rad/s, allows for direct comparison of moduli values. Control pNAM samples had very low G' and G" results with high error, reflective of the weak hydrophilic/hydrophobic interactions between polymer strands [60]. The incorporation of chitosan results in statistically higher moduli among all samples with 40-85× higher storage and 25-35× higher loss moduli in comparison to the control. The higher the concentration of chitosan added, generally the higher the storage and loss moduli. 3-CCN is a notable exception with a slightly lower storage modulus than 1-CCN. The storage and loss moduli of 3-PEC was significantly higher than 3-CCN. The covalently conjugated chitosan has higher moduli in comparison to the polymer network based on ionic interactions which are weaker bonds.

With the storage and loss moduli for a given polymer the damping factor, δ, can be determined:

$$\tan\delta = \frac{G''}{G'}$$

When the damping factor approaches 0° the material acts ideally elastically and as the damping factor approaches 90° the polymer behaves ideally viscous. The pNAM control and 3-CCN have damping factors of 41° implying the materials are more viscous when compared to 1-CCN, 3-PEC and 5-CCN which have damping factors of 24°, 25° and 22° respectively. Again, 3-CCN is different, despite the covalent conjugation, as it is softer in comparison to the ionically crosslinked 3-PEC. Along with the intermediate LCST, the slightly more viscous nature of 3-CCN is desirable for spreading and comfort when applied to the inferior fornix. Therefore, 3-CCN and 3-PEC were selected for being the focus of subsequent hydrogel testing.

Swelling Properties

The swelling ratios of all polymer samples were determined gravimetrically. Dry lyophilized polymer samples were dissolved to 20% (m/v) in PBS. The polymer solutions were then weighed ($M_1$) before being incubated at 37° C. for 24 hours. Following incubation any supernatant expelled from the gel was extracted and the samples were carefully blotted dry with tissue paper and the swollen gels weighed (MS). The equilibrium water content (EWC) of the thermo-gels was also assessed. The dry polymer mass (MD) was compared to the swollen gels following supernatant removal. The equilibrium water content was determined using equation;

$$EWC = \left(\frac{M_S - M_D}{M_S}\right)100$$

Results and Discussion

Figure 7:
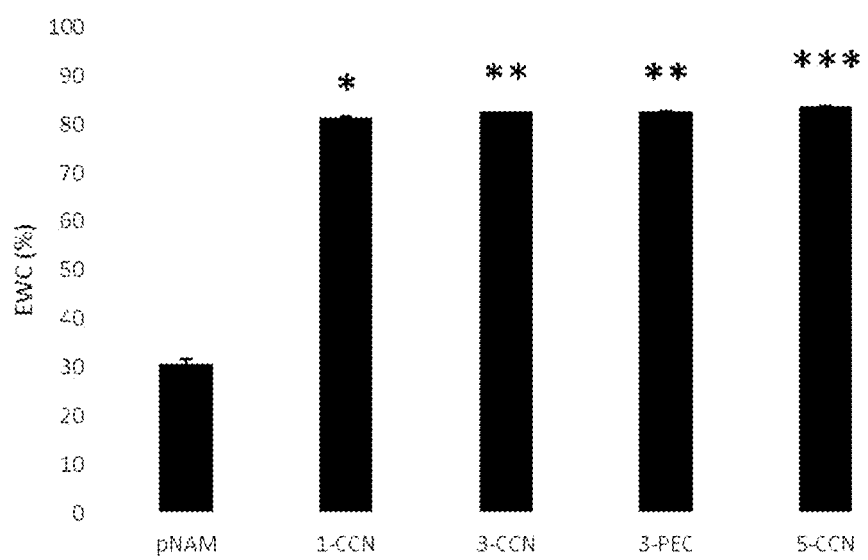
FIG. 7 shows swelling properties of exemplary thermo-gels.

The swelling properties of the polymer networks are shown in FIG. 7. The crosslinking of pNAM with chitosan results in a thermo-gel which undergoes a slight change in volume upon gelation, where all crosslinked networks retain greater than 80% of water content upon gelation. The mass of water retention of the swollen polymer, at a solution concentration of 20% (m/v), is a minimum of 10× higher with the incorporation of chitosan. The high EWC is consistent with previously published work on chitosan crosslinked thermo-gels [11, 61, 62]. With the higher concentration of chitosan crosslinked there is a statistically significant ($p<0.05$) increase in the EWC of the hydrogel networks except between 3-CCN and 3-PEC.

Gravimetric Hydrogel Degradation

The degradation of pNAM, 3-CCN and 3-PEC was conducted at 37° C. 100 mg polymer samples were dissolved to 20 wt/v in PBS before being allowed to gel for 1 hour. Following the initial incubation time, any supernatant was extracted, and the swollen samples were weighed representing time zero (($M_1$)). The gels were then incubated with either 0.5 mL PBS as a control or PBS containing 1.4 mg/mL hen egg white lysozyme to simulate physiological protein concentration. At predetermined time intervals the supernatants were extracted, and the remaining gels weighed (Mw) to determine the degradation by mass loss. The degradation of the polymer samples was then calculated by;

$$\text{Degradation} = \left(\frac{M_W}{M_I}\right)100$$

Results and Discussion

Figure 8:
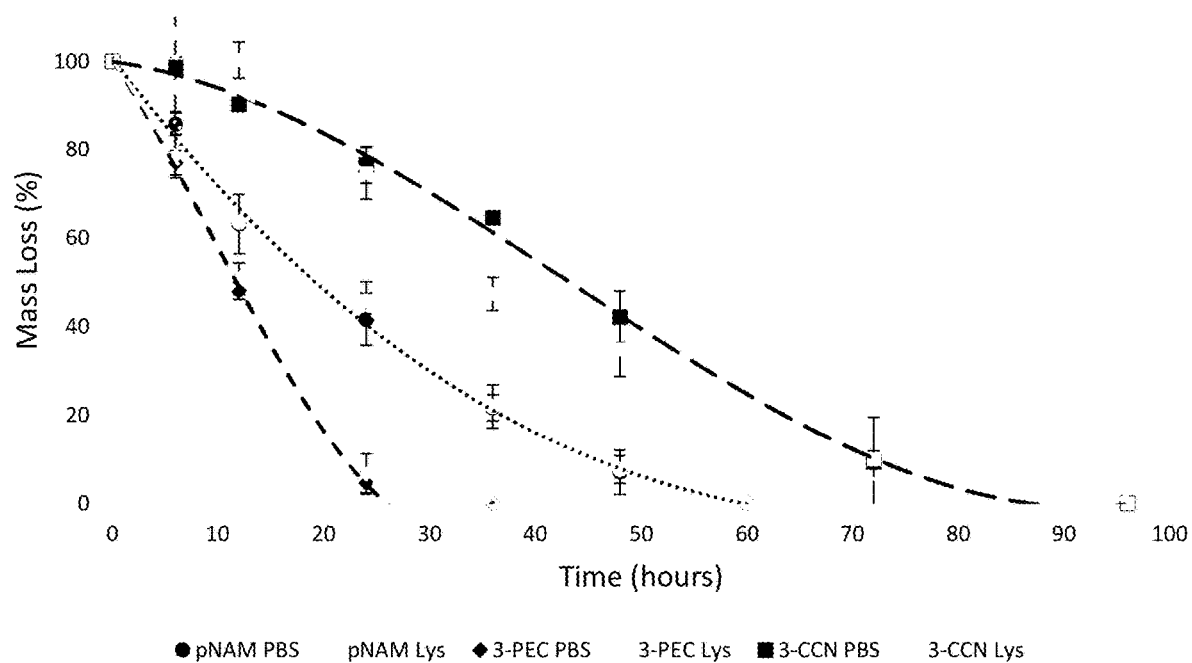
FIG. 8 shows aqueous degradation of exemplary thermo-gels with and without lysozyme.

FIG. 8 shows the hydrogel degradation of pNAM, 3-CCN and 3-PEC over time with or without the enzyme lysozyme (Lys). Despite the gel mechanical strength, the ionic interactions of 3-PEC hydrogels were quickly degraded in the aqueous environment and last just over 24 hours with no statistical influence by lysozyme. Comparatively, the base pNAM thermo-gel degraded over 60 hours, also without a statistically significant influence by lysozyme, which was expected. The 3-CCN samples lasted the longest in the aqueous environment degrading over 96 hours, 4 times longer than 3-PEC and over 1.5 times longer than pNAM. For application to the anterior of the eye, gel survival for 4 days marks a vast improvement compared to conventional, daily use eyedrops. However, no difference was observed for the duration of 3-CCN degradation with or without lysozyme. As it can be seen from the FIG. 8, the 3-CCN samples initially gain mass as the gel swells in supernatant. While not wishing to be limited by theory, this swelling effect, as well as the shear effect encountered with supernatant addition, may cause rapid mechanical degradation of the hydrogel such that the impact of lysozyme on degradation becomes less of a factor. It is important to note that mechanical forces are a big factor in the inferior fornix of the eye with globe movement and tear renewal/drainage [50].

Rheometric Hydrogel Degradation

The degradation of pNAM, 3-CCN and 3-PEC through just the action of the enzyme lysozyme was assessed by comparing gel stiffness after incubation. 100 mg polymer samples were dissolved at 20% wt/v in either PBS, PBS containing 1.4 mg/mL of lysozyme to reflect tear fluid or PBS containing 14 mg/mL lysozyme. The samples were then incubated at 37° C. for 48 hours based on the half-life of lysozyme. Following incubation, the samples were cooled to 4° C. overnight to re-dissolve the hydrogels. Finally, frequency sweeps were conducted at 37° C. to determine gel stiffness and compare the effect of incubating the chitosan-based hydrogels with lysozyme.

Results and Discussion

Figure 9:
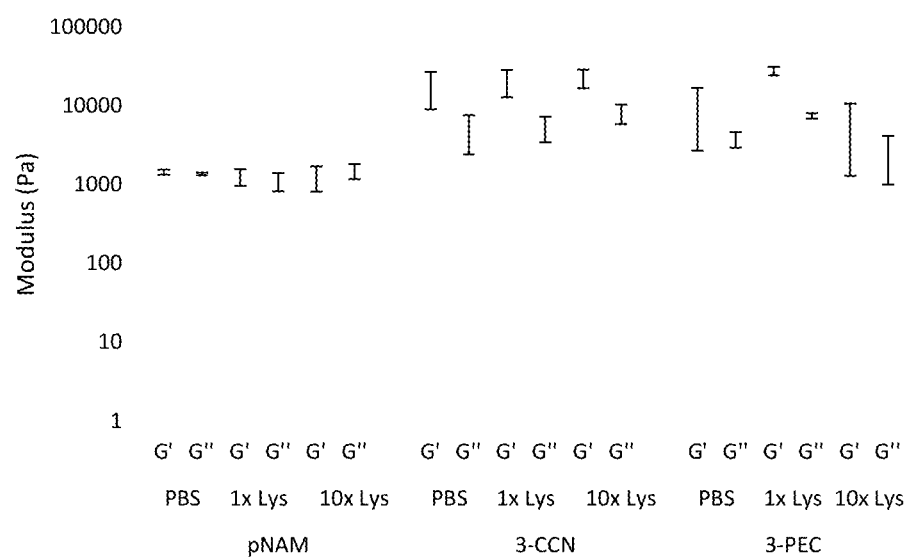
FIG. 9 shows rheological analysis of lysozyme on exemplary thermo-gel degradation.

To determine just the influence of lysozyme on thermo-gel integrity, samples were incubated with or without lysozyme at a given concentration. After incubating for 48 hours the mechanical attributes of the gels were determined by rheology. FIG. 9 compares the moduli from frequency sweeps of pNAM, 3-CCN and 3-PEC after incubation at 1 rad/s. From the data there was no statistical impact on hydrogel mechanical properties after incubation with the tear fluid concentration of lysozyme, or 10× the tear fluid concentration of lysozyme, after 48 hours. This data shows that hydrogel degradation by lysozyme is minimal over this time frame. Therefore, the degradation achieved with an applied supernatant can be attributed fully to mechanical properties such as swelling and applied shear. The chitosan which is utilized in this study was chosen specifically for its low DDA and molecular weight, both of which are attributes that promote lysozyme's breakdown of chitosan. It is possible that with the high degree of polymer interaction with CTS-pNAM, lysozyme is unable to effectively bind to chitosan to degrade it.

Drug Release 100 mg samples of pNAM, 3-CCN and 3-PEC were dissolved at 20% (wt/v) in PBS containing 0.35 mg/mL ketotifen fumarate (KF). The samples were then gelled at 37° C. and allowed to swell for 1 hour before the addition of 0.5 mL pre-warmed PBS supernatant. 200 µL aliquots were removed at set time intervals and replaced with an equal volume of release media. Following collection, the samples were frozen and subsequently lyophilized. The amount of KF released was analyzed by an HPLC. The mobile phase consisted of 60:40 10 mM ammonium acetate (pH 3.5):methanol and was passed over a 0.45 µm nylon filter prior to use [63]. Freeze dried samples were dissolved in 10 mM ammonium acetate (pH 3.5) and passed through a 0.2 µm Nylon filter prior to HPLC quantification. The concentration values determined were assessed against a KF calibration curve with a wavelength maximum of 300 nm.

Results and Discussion

The release of KF from base pNAM polymer, 3-CCN and 3-PEC over seven days, shown in FIG. 10, demonstrated that more drug is released from 3-PEC hydrogels, 59.5±0.5%, compared with the base pNAM or 3-CCN at 50.2±2.5% and 43.3±5.5% respectively. This result correlates with the 3-PEC degrading more quickly than the other hydrogels. 3-CCN released the lowest amount of KF over the testing period again, correlating with degradation profiles. In all cases, the controlled release of KF observed from the thermo-gels represents a significant improvement of the burst noted with conventional topical eyedrops. Overall, release was relatively linear, with a small initial burst.

In Vitro Cytotoxicity Assay

Human corneal epithelial cells (HCEC's) were cultured in keratinocyte serum free medium (Gibco™, Thermo Fischer Scientific) containing 25 mg of bovine pituitary extract and 2.5 µg human recombinant epidermal growth factor (Thermo Fisher Scientific) at 37° C. and 5% CO2. The culture media were changed every 2 days with cells reaching confluence after 7 to 10 days. The cells were passaged at 80-90% confluence.

The cytotoxicity of pNAM, 3-CCN and 3-PEC polymers was assessed using an MTT assay [64]. HCECs were plated into 96-well microtiter plates at a density of 20,000 cells/well. After 24 hours, the culture media was replaced with 200 µL of media containing pNAM, 3-CCN or 3-PEC (n=4) at a concentration of 1% (wt/v), passed through a 0.2 µm syringe filter and UV treated for minimum 12 hours prior to cell exposure. Fresh medium served as a control. After 24 or 48 hours, the gel and media were removed, and the cells washed gently with PBS. The negative control was produced by incubating cells with 1× Triton for three minutes after which the triton was removed, and the cells washed three times with PBS. 3-(4,5-dimethylthiazol-2-yl)-2,5-diphenyltetrazolium bromide (MTT) powder was first dissolved to 5 mg/mL in sterile PBS. 100 µL of medium containing 10% (v/v) MTT solution was added to each well. After 3 hours, any unreacted MTT was removed and replaced with 200 µL of DMSO for 15 minutes. The cell viability was quantified by a SpectraMax® ABS Plus UV-vis micro-plate reader at a wavelength of 570 nm. Cell viability was calculated by:

$$\text{Cell Viability} = \frac{Abs_{sample}}{Abs_{control}}$$

Polymer cytotoxicity was also assessed by Live/Dead staining. Cells were plated and treated as described above for 24 hours. The cells were then stained with a calcein-AM/ethidium homodimer-1 fluorescence kit (Thermo Fisher Scientific) and visualized with an Olympus IX51 inverted fluorescent microscope (Shinjuku, Tokyo, Japan).

Results and Discussion

The cytotoxicity of the pNAM, 3-CCN and 3-PEC polymers as determined by MTT assay is shown in FIG. 11. From the MTT assay it can be determined that the thermo-gelling polymers had low cytotoxicity. For the 24-hour time point, the 3-CCN gels were not statistically different from the positive control (p>0.05) while the 3-PEC performed just below the positive control (p=0.049). At the 48-hour time point, the 3-CCN and 3-PEC samples were not statistically different from the positive control (p>0.05). Notably, the pNAM base polymer yields a statistically higher cell viability (p<0.05) than the positive control or 3-CCN and 3-PEC samples suggesting the cell-gel interactions are favorable for growth in the given conditions.

The response of HCEC cells following thermo-gel treatment is visualized in FIG. 12 with Live/Dead staining After 24 hours, none of the applied thermo-gels resulted in significant visual cell death. Following incubation with 3-CCN, the cell morphology was more spherical compared to the other gel and control samples. This suggests that the cells are in a more stressed state following treatment with 3-CCN which reflects a change in cellular transport phenomena as the cells are covered by the covalently crosslinked thermo-gel.

In Vivo Safety Analysis

Animal studies were performed in compliance with protocols approved by the Animal Research Ethics Board at McMaster University in accordance with the regulations of the Animals for Research Act of the Province of Ontario and the guidelines of the Canadian Council on Animal Care. Five, 9-month-old female Brown Norway Rats (Charles River, Wilmington, Massachusetts, USA) were utilized to test the in vivo compatibility of pNAM, 3-CCN and 3-PEC gels. The rats were anesthetized with gaseous isoflurane before the application of 10 μL of pNAM, 3-CCN, 3-PEC or PBS as a control to both eyes of one rat. The thermo-gel samples were UV treated for 12 hours prior to application. The samples were allowed to gel against the surface of the rat eyes for a minimum of a half hour prior to the reversal of anaesthesia and the onset of blinking After 24 hours, the rats were euthanized, and the eyes were harvested and fixed in 4% paraformaldehyde overnight at 4° C. and then stored in 70% ethanol. Samples were processed and embedded in paraffin (Paraplast Tissue Embedding Media, Thermo Fischer Scientific). Finally, serial sections were cut to 4 μm in thickness and used for hematoxylin and eosin (H&E) staining and visualized with an Olympus BX51 inverted microscope. Corneal thickness measurements were taken from H&E-stained slides using open-source ImageJ (NIH) software.

Results and Discussion

The effect of the thermo-gels on rat corneas was assessed by H&E staining (FIG. 13). From the histological staining, it was observed that there was no difference in inflammation or appearance of inflammatory cells in the cornea and anterior chamber between PBS treated controls (13A, B) and thermo-gel treated (13C-H) rats after 24 hours. Based on measurement of the corneal epithelium, stroma, and Descemet's membrane and endothelium, there was no apparent difference in morphology of control corneas or those treated with pNAM, 3-CCN or 3-PEC thermo-gels. From these results, the thermo-gels do not produce an inflammatory response or induce morphological change from short term application.

Example 2: pNAM Polymer or pNAMP Polymer+80-130 kDa Chitosan Thermo-Gel

Materials

Chitosan (MW=80-200 kDa, DDA=70%) was purchased from Heppe Medical Chitosan (Halle, Saxony-Anhalt, Germany) and used as received. N-isopropylacrylamide (NIPAAm; 97%) was purchased from Sigma-Aldrich (Oakville, Ontario, Canada) and purified by recrystallization from toluene with n-hexane. Acrylic Acid (AA; 99%) was purchased from Sigma-Aldrich and was purified by passing through a packed column containing Sigma-Aldrich inhibitor remover to remove the inhibitor 4-methoxyphenol. Methyl methacrylate (MMA; 99%), Benzoyl Peroxide (BPO; Luperox®, 98%), N-(3-Dimethylaminopropyl)-N'-ethylcarbodiimide hydrochloride (EDC; BioXtra), 2-mercaptoethanol (99%), atropine sulfate monohydrate (97%) and 2-(N-morpholino)ethanesulfonic acid (MES; free acid) were purchased from Sigma-Aldrich and used as received. 1,4-Dioxane, n-hexane, toluene, anhydrous diethyl ether and tetrahydrofuran (THF) were purchased from VWR (Radnor, Pennsylvania, USA) and used as received. Milli-Q grade deionized water was prepared using a Barnstead Diamond™ water purification system (Thermo Fischer Scientific, Waltham, Massachusetts, USA). 10× Phosphate buffered saline (PBS) was purchased from BioShop® (Burlington, Ontario, Canada) and diluted with deionized water to 1× (pH 7.4) for all experiments. All other compounds were purchased from Sigma Aldrich (Oakville, Ontario, Canada) unless otherwise specified.

Pyridyl Disulfide Ethylmethacylate (PDSMA) Monomer Synthesis

The PDSMA monomer was synthesized based on protocols previously reported in literature [65, 66]. One gram of pyridyl disulfide was dissolved in methanol to a concentration of 83.3 mg/mL. 7.7 molar equivalents of acetic acid was then added dropwise followed by 0.72 molar equivalents of mercaptoethanol dissolved to 0.43 mM in ethanol. The reaction then proceeded overnight under constant stirring. Following the reaction, the produced intermediate 2-(pyridin-2-yldisulfaneyl)ethan-1-ol (PDSOH) was then extracted and column purified. Purified PDSOH was then dissolved in anhydrous dichloromethane to a concentration of 25 mg/mL. 2 molar equivalents of N,N-diisopropylethylamine was then added to the reaction mixture before being placed on an ice bath. Finally, 1.2 molar equivalents of methacryloyl chloride dissolved in an equal volume of anhydrous (DCM) to the reaction mixture is added dropwise and reacted for 12 hours. The pyridyl disulfide ethyl methacrylate product was extracted, and column purified.

Poly(n-isopropylacrylamide-co-Acrylic Acid-co-methyl methacrylate-co-pyridyl disulfide ethylmethacrylate) (pNAMP) Synthesis The free radical synthesis of the base terpolymer pNAM and functional tetrapolymer pNAMP followed the protocol described in Example 1. The synthetic scheme of pNAMP synthesis is visualized in FIG. 14a). Four polymers were produced containing 0, 1, 2 and 3 mol % PDSMA. These samples are denoted as pNAM, pNAMP-1, pNAMP-2, and pNAMP-3 respectively. To produce 1 g of pNAMP-3, 834.0 mg (7.37 mmol) of recrystallized NIPAAm, 12.5 mg (0.17 mmol) uninhibited AA, 86.8 mg (0.87 mmol) of MMA, 66.4 mg (0.26 mmol) of PDSMA and 21.1 mg of BPO (0.10 mmol) were dissolved in a round bottom flask containing 10 mL of 1,4-dioxane:deionized water (9:1 v/v) to produce a 10% (wt/v) monomer solution. The flask was then sealed, and the oxygen purged with nitrogen for 20 minutes. The reaction than proceeded at 70° C. for 24 hours. Following polymerization, the polymer was precipitated twice into 800 mL of chilled anhydrous ethyl ether. The resulting pNAMP-3 powder was collected by vacuum filtration and dialyzed against 4 L of deionized water using a Membra-Cel® 14 kDA MWCO cellulose membrane (Viskase®, Lombard, Illinois, USA) for three days. After dialysis the polymer was lyophilized using a Labconco™ FreeZone 2.5 benchtop freeze drier (Kansas City, Missouri, USA) and stored at −20° C. The composition of the polymers was determined by $^1$H NMR using a Bruker© 600 MHz Spectrometer (Billerica, Massachusetts, USA). All samples were dissolved in DMSO-D$_6$ for analysis. The pNAMP polymer molecular weights were determined by a Polymer Laboratories PL-50 gel permeation chromatographer (GPC; Church Streton, Shropshire, UK) fitted with three Phenomenex Phenogel™ columns; pore sizes 100, 500 and 104 Å (Torrance, California, USA) at room temperature. Dimethylformamide containing 5 mM lithium bromide was used as the eluent. All samples were filtered through a 0.2 μm PTFE syringe filter prior to quantification. Linear polyethylene glycol standards provided by Polymer Laboratories were utilized for molecular weight calibration.

Results and Discussion

The composition of the base thermo-gelling polymer was determined utilizing $^1$H NMR. The structure of pNAMP-3 is visualized in FIG. 15, the tertiary NH of the isopropyl tail of NIPAAm occurs at 3.84 ppm (A), the OH of AA at 12.0 ppm (B), the aromatic pyridine of PDMSA as multiple peaks from 7.25-8.50 ppm (C-E) and the methyl tail of MMA as a doublet at 3.49 and 3.50 (F).

The composition of the produced thermo-gels is listed in Table 1.

| Polymer | Theoretical Composition | Determined Composition |
| --- | --- | --- |
| pNAM | 88:2:10 | 86.86:1.52:11.64 |
| pNAMP-1 | 87:2:10:1 | 87.21:1.45:10.72:0.63 |
| pNAMP-2 | 86:2:10:2 | 85.60:1.49:11.17:1.74 |
| pNAMP-3 | 85:2:10:3 | 84.42:1.61:11.37:2.60 |

Chitosan Crosslinked pNAMP Networks

The synthesis of covalently crosslinked chitosan networks of pNAMP (CTS-pNAMP) followed similar protocols to those described in Example 1 and is visualized in FIG. 14b). For all the produced crosslinked networks a concentration of 3% (wt/wt) of chitosan/pNAMP was utilized. Briefly, 30 mg of chitosan was dissolved in 30 mL of 10 mM MES buffer, adjusted to pH 4.7 with 0.1 N NaOH, and heated at 45° C. under constant stirring. After 5 hours, the chitosan solution was filtered with a 0.45 μm syringe filter to remove any large aggregates and used to dissolve 1 g of pNAMP powder. Finally, 61.6 mg of EDC was dissolved in a minimum volume of MES buffer and added dropwise to the chitosan/pNAMP solution and reacted for 24 hours under constant stirring. The produced CTS-pNAMP was then dialyzed against 4 L of deionized water using Spectrum Labs 3.5 kD MWCO Spectra/Por Grade regenerated cellulose dialysis membrane (VWR, Radnor, Pennsylvania, USA) for three days. Samples were finally lyophilized and stored at −20° C.

The CTS-pNAMP networks were characterized by $^1$H NMR (FIG. 16), all samples were dissolved in D$_2$O.

Cysteamine Conjugation of CTS-pNAMP

For treatment of cystinosis, cysteamine was conjugated to CTS-pNAMP thermo-gels by a disulfide exchange reaction, visualized in FIG. 14c). CTS-pNAMP samples were dissolved to a concentration of 3% (wt/v). Cysteamine was dissolved to a concentration of 10 mg/mL and the pH adjust to 6.5 using 0.1 N HCl. The cysteamine was added dropwise to the CTS-pNAMP solution under constant stirring and allowed to react for 24 hours. The resulting CTS-pNAMP-C was then dialyzed against 4 L of deionized water using Spectrum Labs 3.5 kD MWCO Spectra/Por Grade regenerated cellulose dialysis membrane, for three days. Samples were then lyophilized and stored at −20° C. The conjugation of cysteamine was measured by the evolution of pyridine using a SpectraMax® ABS Plus UV-vis micro-plate reader (Molecular Devices, San Jose, California, USA) at a wavelength of 343 nm.

Results and Analysis

The crosslinking of chitosan to the base pNAMP thermo-gel was accomplished by the covalent conjugation of the primary amines of chitosan to the carboxylic acids of AA through the carbodiimide crosslinker EDC. AA was incorporated into the base polymer backbone to facilitate crosslinking with chitosan. As the carboxylic acids of AA along the polymer backbone are conjugated to chitosan, the pH of the polymer networks increases. When dissolved at a concentration of 10% (wt/v) the base thermo-gelling polymers have a pH of 5.17, low due to the pKa of AA, while the chitosan crosslinked networks have a pH 6.53. A pH of 6.53 is close to the maximum pH achievable for a chitosan containing network without causing the precipitation of chitosan. In this work a chitosan concentration of 3% (wt/wt) chitosan/pNAMP was utilized because of the favorable mechanical and thermo-gelling properties established from previous work, as outlined in Example 1. From the previous investigation, a higher concentration of AA was incorporated into the base polymer backbone, 5 mol % compared to 2 mol %. This higher concentration of AA led to lower solution pH values for both the base and chitosan crosslinked thermo-gels. By lowering the amount of AA in the base polymer backbone higher pH values were produced closer to physiologic pH.

The chitosan crosslinking and subsequent conjugation of cysteamine to pNAMP-3 was characterized utilizing $^1$H NMR and shown in FIG. 16. The conjugation of chitosan is shown in both spectra by the secondary amine peak at 2.83 ppm. CTS-pNAMP-3 contains the aromatic peaks of pyridine occurring at 7.27-8.37 ppm. The successful conjugation of cysteamine is visualized by the reduction of aromatic peaks as pyridine is removed and the incorporation of the peaks at 3.34 and 2.95 ppm corresponding to carbons adjacent to the thiol and tertiary amine respectively.

The chitosan crosslinked thermo-gels were characterized by FTIR from 500 to 4000 cm$^{-1}$. The FTIR spectra of pNAM and CTS-pNAM is visualized in FIG. 17. The uncrosslinked pNAMP-3 contains the characteristic monomer peaks of NIPAAm at 3300 cm$^{-1}$ (NH stretch), 1640 cm$^{-1}$ (C═O stretch, amide I) and 1530 cm$^{-1}$ (NH bend, amide II), AA seen at 1726 cm-1 (carbonyl C═O stretch), MMA at 1171 cm-1 (ester C—O) and 1130 cm$^{-1}$ (unconjugated ester —CO—O—CH$_3$ stretch). With the incorporation of chitosan two new peaks are observed at 1077 and 1039 cm$^{-1}$ reflecting the C—O—C and C—O stretches of chitosan.

Rheological Analysis of Materials Properties

The material properties of base pNAM, CTS-pNAM were assessed by a Discovery HR-2 hybrid rheometer (Waters™, Newcastle, Delaware, USA). All samples were tested at a concentration 10% (w/v) in PBS. Stress and frequency sweeps were conducted utilizing a 20 mm parallel Peltier plate. Stress sweeps were utilized to determine the linear viscoelastic region of the base pNAM and CTS-pNAM at 37° C. Frequency sweeps were conducted to quantify the effect of chitosan crosslinking on pNAM and CTS-pNAM.

Temperature ramps were conducted at a rate of 1° C./min from 15 to 45° C., utilizing a 20 mm 1° cone and Peltier plate assembly. The LCST was defined as the temperature in which both the storage and loss modulus statistically increase above the baseline measurement. Temperature ramps were conducted on the base pNAM and CTS-pNAM as well as the final cysteamine conjugated networks CTS-pNAMP-C1, CTS-pNAMP-C2 and CTS-pNAMP-C3.

Results and Discussion

Strain sweeps and frequency sweeps were conducted on the base pNAM and CTS-pNAM thermo-gels to study the effect of chitosan crosslinking. The strain sweep analysis is shown in FIG. 18a). From the strain sweep analysis, the base pNAM polymer fail after an applied oscillation strain of 15% while the crosslinked CTS-pNAM did not fail up to 100% applied oscillation strain. For subsequent testing, an oscillation strain of 0.1% was utilized as it was well within the linear viscoelastic region of both thermo-gels. Frequency sweeps were conducted to further assess the influence of chitosan crosslinking, as shown in FIG. 18b). The uncrosslinked pNAMP displays shear thickening while the properties of CTS-pNAM remain independent of angular frequency. The CTS-pNAM has greater modulus values compared to pNAM especially as lower angular frequencies. The damping factor (6), determined by:

$$\tan\delta = \frac{G''}{G'}$$

The damping factor relates modulus values to material behavior; when the damping factor approaches 90° the polymer behaves ideally viscous and as the damping factor approaches 0° the material acts ideally elastically. The damping factor for pNAM and CTS-pNAM calculated from the frequency sweep is shown in FIG. 18c). pNAM has a damping factor of approximately 40° compared to 10° of CTS-pNAM illustrating that following chitosan crosslinking the thermo-gels behave much more elastic.

Example 1 examined the effect of chitosan crosslinking with a shorter chitosan crosslinker, 10-50 kDa and the subsequent rheologic properties. In this study utilizing a larger chitosan, 80-130 kDa, with a scaled concentration of the EDC crosslinker, the resulting networks were found to have lower modulus values. In the previous study, CTS-pNAM containing 3% (wt/wt) of the shorter chitosan had a storage and loss modulus of greater than 10 000 and 100 Pa respectively while in the current study utilizing the larger molecular weight chitosan the storage and loss modulus are greater than 100 and 10 Pa respectively. While not wishing to be limited by theory, this decrease in mechanical properties is attributable to the lower degree of crosslinking produced when using larger molecular weight chitosan and keeping the moles of EDC constant. Thermo-gels produced through physical ionic interactions using the lower molecular weight chitosan had similar modulus values to those produced through EDC chemistry, a full order of magnitude greater than the thermo-gels produced in this study. Therefore, the physical properties of the chitosan, particularly the molecular weight, have an impact on mechanical properties.

The LCST of the base pNAM and CTS-pNAM as well as the cysteamine modified thermo-gels were determined by temperature ramps. The determined LCST values are displayed in Figured 19. The LCST of the thermo-gel increased after crosslinking with chitosan although this was not statistically significant (p=0.085). Further conjugation of cysteamine after chitosan crosslinking resulted in an increase in LCST. CTS-pNAMP-C3 had a statistically higher LCST compared to CTS-pNAM while both CTS-pNAMP-C1 and CTS-pNAMP-C2 were not statistically different from CTS-pNAM.

Analysis of Muco-Adhesive Properties

The mucoadhesive properties of the prepared thermogels were determined by rheological synergism [34, 67].

$$\eta_{synergism} = \eta_{mix} - (\eta_{thermo\text{-}gel} + \eta_{mucin})$$

An equal volume of 6% (wt/wt) mucin dispersion was mixed with either dissolved thermo-gel at 20% (wt/v) or buffer as control for one hour prior to testing (final mucin concentration of 3% (wt/wt) and thermo-gel 10% (wt/v) respectively). Viscosity was measured by a flow sweep at a shear rate of 0.1 to 100 1/s utilizing a rheometer fitted with a 20 mm 1° cone and Peltier plate assembly at 4° C. Viscosity measurement was conducted for all the produced thermo-gels prior to cysteamine conjugation.

The extent of pNAMP adhesion to mucin was assessed by the evolution of pyridine using UV-vis. 0.05% (wt/v) pNAMP was mixed with either PBS, 0.015% (wt/wt) mucin, or an equimolar concentration of the small thiol bearing compound mercaptoethanol. The amount of pyridine released by disulfide exchange with mucin was compared to the control mercaptoethanol.

$$\text{Pyridine Evolution} = \left(\frac{\text{Abs}_{Mucin}}{\text{Abs}_{Mercaptoethanol}}\right)100$$

The evolution of pyridine was quantified by UV-vis at a wavelength of 343 nm.

Results and Discussion

The rheological synergism of the thermo-gels is displayed in FIG. 20. Comparing the uncrosslinked polymers containing various concentrations of PDSMA, there was no statistically significant impact of PDSMA concentration on muco-adhesive properties. Comparing base pNAM to CTS-pNAM the incorporation of chitosan improved the muco-adhesive properties by greater than a full order of magnitude. Chitosan is well established to be muco-adhesive through charge interaction. By varying the concentration of PDSMA after chitosan crosslinking a further improvement of muco-adhesive properties is demonstrated. Both CTS-pNAMP-2 and CTS-pNAMP-3 increased the muco-adhesion by another full order of magnitude compared to CTS-pNAM. CTS-pNAMP-1 did not statistically increase the muco-adhesion compared to CTS-pNAM. Although changing the concentration of PDSMA in the base polymer did not have a significant impact on muco-adhesion, changing the concentration after crosslinking did have a significant effect showing that these muco-adhesive properties also display synergism.

These results demonstrate that the muco-adhesive properties of the thermo-gels can be increased by incorporation of chitosan or the disulfide monomer PDSMA, but the degree of muco-adhesion can be controlled by changing the concentration of these components. This is very relevant for designing a material to be applied to the surface of the eye, or another mucosal surface, as adhesion directly impacts retention.

The degree of polymer interaction with mucin by disulfide bonding was measured through pyridine evolution. Comparing the amount of pyridine released after mixing with mucin to that after mixing with mercaptoethanol yields an estimate for interaction. The value of pyridine release is summarized in Table 2. From these results, at least half of the pyridine is released following incubation with mucin. The amount of pyridine released did not scale with the concentration of PDSMA in the polymer backbone, such that an increase in PDSMA will result in an increase of disulfide bonding with mucin.

TABLE 1

Evolution of pyridine from incubation with mucin compared to mercaptoethanol

| Thermo-gel | Pyridine Evolution (%) |
|---|---|
| pNAM | 0 |
| pNAMP-1 | 48.4 |
| pNAMP-2 | 70.3 |
| pNAMP-3 | 60.7 |

Thermo-Gel Swelling

The swelling properties of the pNAM and CTS-pNAM were assessed gravimetrically at a concentration of 10% (wt/v). The dissolved solutions were weighed ($M_1$) before being allowed to gel at 37° C. After 24 hours, the gels were blotted dry and reweighed (MF). The swelling ratio was calculated as the ratio of gelled mass to dissolved solution.

$$\text{Gel Swelling} = \left(\frac{M_F}{M_I}\right)100$$

Results and Discussion

The swelling profile of pNAM and CTS-pNAM are displayed in FIG. 21. Following chitosan crosslinking, the networks are significantly more volume retentive holding 57.5% of the volume compared to 28.1% without crosslinking. These materials underwent significantly more syneresis compared to thermo-gels produced in Example 1 which were close to fully volume retentive.

Determination of Thermo-Gel Enzymatic Degradation

The gravimetric degradation of pNAM and CTS-pNAM was conducted at 37° C. 50 mg of the respective thermo-gel were dissolved at 10% (wt/v) and allowed to gel for 24 hours prior to testing. Following the initial incubation (t=0), the samples were blotted dry, and the initial mass measured ($M_I$). The dry gels were then incubated with 0.5 mL of either PBS or PBS containing the physiologic concentration of hen egg white lysozyme. At given time intervals, the supernatants were extracted, and the gel mass measured (MT). The degradation of the thermo-gels was calculated as the mass at a predetermined time interval to the initial gel mass.

$$\text{Degradation} = \left(\frac{M_W}{M_I}\right)100$$

The action of lysozyme on the degradation of the produced thermo-gels was also quantified by measurement of the viscosity following incubation. 50 mg of the respective thermo-gel were dissolved at 10% (wt/v) in either PBS or PBS containing the physiologic concentration of lysozyme. The samples were then gelled at 37° C. for 48 hours. After incubation, the samples were cooled back to solution and the viscosity measured by rheometric analysis utilizing a flow sweep with a 20 mm 1° cone and Peltier plate at 4° C.

Results and Discussion

The degradation of pNAM and CTS-pNAM in both PBS and PBS containing the physiological concentration of lysozyme is displayed in FIG. 22. Both the pNAM and CTS-pNAM were fully degraded after 4 days with lysozyme whereas both thermo-gels remained after 12 days after incubation with just PBS. FIG. 22 shows the rheological determination onto the impact of lysozyme on thermo-gels. The viscosity of pNAM solution was not statistically different following 48-hour incubation whereas the CTS-pNAM solution viscosity displayed a statistically significant reduction in viscosity after incubation with lysozyme. From FIG. 22a) and FIG. 22b), it can be determined that lysozyme had enzymatic action on CTS-pNAM although not on pNAM. For pNAM, while not wishing to be limited by theory, the degradation noted by lysozyme likely has to do with the charge interaction of positively charge lysozyme with the negatively charged pNAM. As hydrophilic lysozyme associates with and penetrates the pNAM thermo-gel it increases the LCST causing degradation. For CTS-pNAM the change in viscosity following incubation with lysozyme shows that the mode of degradation is enzymatic as the viscosity of the network is lowered as chitosan is cleaved.

Compared to the studies above with a lower molecular weight chitosan, utilizing a larger molecular weight chitosan crosslinker results in enzymatic degradation by lysozyme while utilizing a lower molecular weight chitosan did not result in statistical degradation by lysozyme. Conventionally, utilizing a lower molecular weight of chitosan results in greater degradation by lysozyme [10, 12]. However, from the present research utilizing a higher molecular weight chitosan promotes degradation by lysozyme which, while not wishing to be limited by theory, is likely attributable to promoting lysozyme docking by reducing the number of crosslinks between chitosan and the base polymer.

Pyridine Release by Mucin Conjugation

The release of pyridine from CTS-pNAMP thermo-gels following incubation with mucin is measured by UV-vis. 0.8 mL of 3% (wt/wt) mucin is added to a 1 mL Spectra/Por Float-A-Lyzer® G2 with a 3.5-5 kDa MWCO placed in a 5 mL of PBS and incubated at 37° C. 0.2 mL of thermo-gel dissolved at 10% (wt/v) is then pipetted into the mucin solution and allowed to gel for 5 minutes. 1 mL of PBS supernatant is removed at set time intervals and replaced with an equal volume of release media. The absorbance of pyridine is measured at 343 nm.

Atropine Release

The release of the drug Atropine from the produced thermo-gels is analyzed by an Agilent 1260 Infinity II high performance liquid chromatographer (HPLC; Santa Clara, California, USA). 50 mg of the respective hydrogel is dissolved at 10% (wt/v) in PBS and gelled for one hour at 37° C. before the addition of 0.5 mL of prewarmed PBS containing the physiologic concentration of lysozyme (t=0).

In Vitro Cytotoxicity Determination

Human corneal epithelial cells (HCECs) were utilized for the in vitro analysis of the produced thermo-gels. HCECs were cultured with keratinocyte serum free medium (Gibco™, Thermo Fischer Scientific) containing 25 mg of bovine pituitary extract and 2.5 μg human recombinant epidermal growth factor (Thermo Fisher Scientific) at 37° C. and 5% CO2. The effect of thermo-gel incubation with HCECs was assessed by Live/Dead staining. HCECs were seeded at a concentration of 20 000 cells/well into 96-well microtiter plates. After 24 hours culture media was removed, and the cells were treated with either fresh media or media containing 1% (wt/v) thermo-gel, UV treated for minimum 12 hours prior to cell exposure. Following incubation for 24 or 48 hours the gel containing media was removed and the cells washed with PBS. As a negative control, cells were treated with 1× Triton for three minutes and subsequently washed three times with PBS. Finally, the cells were then stained with a calcein-AM/ethidium homodimer-1 fluorescence kit (Thermo Fisher Scientific) and visualized with an Olympus IX51 inverted fluorescent microscope (Shinjuku, Tokyo, Japan).

The MTT assay was utilized to quantify the cytotoxicity of thermo-gel incubation. Cells were seeded and treated as described above. 3-(4,5-dimethylthiazol-2-yl)-2,5-diphenyltetrazolium bromide (MTT) powder was dissolved to 5 mg/mL in PBS. The MTT solution was then diluted to 10% (v/v) in culture media. After 24 or 48 hours, the treated cells were incubated with 100 µL of the diluted MTT solution. The cells incubated for 3 hours. After incubation, the MTT media was removed and 200 µL of DMSO was added to dissolve the formazan crystals for 15 minutes. The cytotoxicity was measured by UV-vis at a wavelength of 570 nm.
Results and Discussion The MTT analysis of the pNAM and CTS-pNAM are shown in FIG. 23. Crosslinked CTS-pNAM thermo-gels were not statistically different (p>0.05) from untreated cells. Base pNAM treated cells resulted in an increase in viability compared to untreated cells, statistically significant at 48 hours (p<0.05), suggesting the cells prefer the environment of the uncrosslinked thermo-gel. After 24 and 48 hours the MTT assay demonstrates that the produced thermo-gels are nontoxic.

The Live/Dead assay of pNAM and CTS-pNAM is shown in FIG. 24. pNAM and CTS-pNAM treated cells do not result in significant cell death or morphological change after 24 and 48 hours. The Live/Dead staining further corroborates the MTT testing that the produced thermo-gels are not cytotoxic.
In Vivo Safety Analysis Animals were cared for and analyzed in compliance with protocols approved by the Animal Research Ethics Board at McMaster University in accordance with the regulations of the Animals for Research Act of the Province of Ontario and the guidelines of the Canadian Council on Animal Care. 12, 19-week-old female Brown Norway Rats (Charles River, Wilmington, Massachusetts, USA) were utilized to test the safety of pNAM, CTS-pNAM and CTS-pNAMP-C2 thermo-gels. The thermo-gel samples were dissolved to 10% (wt/v) in PBS and UV treated for 12 hours prior to application. The rats were anesthetized with gaseous isoflurane before the application of 10 µL of PBS, pNAM, CTS-pNAM or CTS-pNAMP-C2 every day for one week; three rats per test group. The produced materials were allowed to gel and stay on the surface of the day for 1 hour prior to the reversal of anesthesia and the onset of rat blinking. At days 1, 3 and 5 the cornea was assessed utilizing a Pheonix MICRON™ Optical Coherence Tomography imaging system (OCT; Owens Drive, Pleasanton, California, USA) as well as by fluorescence staining to measure corneal disruption.
Results and Discussion The OCT measurement of rat corneal thickness followed by daily treatment with 1×PBS, pNAM, CTS-pNAM or CTS-pNAMP-C2 for one week is shown in FIG. 25. There was no statistical difference in corneal thickness across treatment groups over time except for a slight thickening with pNAM and CTS-pNAM groups after one week of treatment.
Statistical Analysis Error bars represent the standard deviation. Student T-tests based on two tailed distribution and unequal variance was utilized to determine statistical significance.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE APPLICATION

[1] M. Shaker and E. Salcone, "An update on ocular allergy," *Current Opinion in Allergy and Clinical Immunology*, vol. 16, no. 5, pp. 505-510, 2016.

[2] A. Leonardi and L. Quintieri, "Olopatadine: a drug for allergic conjunctivitis targeting the mast cell," *Expert Opinion on Pharmacotherapy*, vol. 11, no. 6, pp. 969-981, 2010.

[3] A. F. Clark and T. Yorio, "Ophthalmic drug discovery," *Nature Reviews Drug Discovery*, vol. 2, no. 6, pp. 448-459, 2003.

[4] J. W. Shell, "Pharmacokinetics of topically applied ophthalmic drugs," *Survey of ophthalmology*, vol. 26, no. 4, pp. 207-218, 1982.

[5] A. A. Azari and N. P. Barney, "Conjunctivitis: a systematic review of diagnosis and treatment," *Jama*, vol. 310, no. 16, pp. 1721-1730, 2013.

[6] T. Irimia et al., "Chitosan-Based In Situ Gels for Ocular Delivery of Therapeutics: A State-of-the-Art Review," *Mar Drugs*, vol. 16, no. 10, Oct. 9, 2018, doi: 10.3390/md16100373.

[7] E. Szymańska and K. Winnicka, "Stability of chitosan—a challenge for pharmaceutical and biomedical applications," *Marine drugs*, vol. 13, no. 4, pp. 1819-1846, 2015.

[8] E. AINE and P. MÖRSKY, "Lysozyme Concentration in Tears-Assessment of Reference Values in Normal Subjects," *Acta ophthalmologica*, vol. 62, no. 6, pp. 932-938, 1984.

[9] R. Sariri and H. Ghafoori, "Tear proteins in health, disease, and contact lens wear," *Biochemistry (moscow)*, vol. 73, no. 4, pp. 381-392, 2008.

[10] J. Li, Y. Du, and H. Liang, "Influence of molecular parameters on the degradation of chitosan by a commercial enzyme," *Polymer Degradation and Stability*, vol. 92, no. 3, pp. 515-524, 2007.

[11] L. J. Luo, C. C. Huang, H. C. Chen, J. Y. Lai, and M. Matsusaki, "Effect of deacetylation degree on controlled pilocarpine release from injectable chitosan-g-poly(N-isopropylacrylamide) carriers," *Carbohydr Polym*, vol. 197, pp. 375-384, Oct. 1, 2018, doi: 10.1016/j.carbpol.2018.06.020.

[12] K. Tomihata and Y. Ikada, "In vitro and in vivo degradation of films of chitin and its deacetylated derivatives," *Biomaterials*, vol. 18, no. 7, pp. 567-575, 1997.

[13] L. Popa, M. V. Ghica, C. E. Dinu-Pirvu, and T. Irimia, "Chitosan: A Good Candidate for Sustained Release Ocular Drug Delivery Systems," in *Chitin-Chitosan—Myriad Functionalities in Science and Technology*, 2018, ch. Chapter 14.

[14] P. Sacco, F. Furlani, G. De Marzo, E. Marsich, S. Paoletti, and I. Donati, "Concepts for Developing Physical Gels of Chitosan and of Chitosan Derivatives," *Gels*, vol. 4, no. 3, Aug. 9, 2018, doi: 10.3390/gels4030067.

[15] Y. H. Cheng et al., "Thermosensitive chitosan-based hydrogel as a topical ocular drug delivery system of latanoprost for glaucoma treatment," *Carbohydr Polym*, vol. 144, pp. 390-9, Jun. 25, 2016, doi: 10.1016/j.carbpol.2016.02.080.

[16] A. S. Hoffman, "4. Poly (NIPAAm) revisited-it has been 28 years since it was first proposed for use as a biomaterial: Original research article: Applications of thermally reversible polymers hydrogels in therapeutics and diagnostics, 1987; thermally reversible hydrogels: II. Delivery and selective removal of substances from aqueous solutions, 1986; a novel approach for preparation of pH-sensitive hydrogels for enteric drug delivery, 1991," *Journal of controlled release: official journal of the Controlled Release Society*, vol. 190, p. 36, 2014.

[17] S. Lanzalaco and E. Armelin, "Poly (n-isopropylacrylamide) and copolymers: A review on recent progresses in biomedical applications," *Gels*, vol. 3, no. 4, p. 36, 2017.

[18] Z. Cui, B. H. Lee, C. Pauken, and B. L. Vernon, "Degradation, cytotoxicity, and biocompatibility of NIPAAm-based thermosensitive, injectable, and bioresorbable polymer hydrogels," *J Biomed Mater Res A*, vol. 98, no. 2, pp. 159-66, August 2011, doi: 10.1002/jbm.a.33093.

[19] M. Patenaude and T. Hoare, "Injectable, Degradable Thermoresponsive Poly(N-isopropylacrylamide) Hydrogels," *ACS Macro Letters*, vol. 1, no. 3, pp. 409-413, 2012, doi: 10.1021/mz200121k.

[20] S. D. Fitzpatrick, M. Jafar Mazumder, F. Lasowski, L. E. Fitzpatrick, and H. Sheardown, "PNIPAAm-grafted-collagen as an injectable, in situ gelling, bioactive cell delivery scaffold," *Biomacromolecules*, vol. 11, no. 9, pp. 2261-2267, 2010.

[21] S. D. Fitzpatrick, M. J. Mazumder, B. Muirhead, and H. Sheardown, "Development of injectable, resorbable drug-releasing copolymer scaffolds for minimally invasive sustained ophthalmic therapeutics," *Acta biomaterialia*, vol. 8, no. 7, pp. 2517-2528, 2012.

[22] M. J. Mazumder, S. D. Fitzpatrick, B. Muirhead, and H. Sheardown, "Cell-adhesive thermogelling PNIPAAm/hyaluronic acid cell delivery hydrogels for potential application as minimally invasive retinal therapeutics," *Journal of biomedical materials research Part A*, vol. 100, no. 7, pp. 1877-1887, 2012.

[23] B. Muirhead, S. Fitzpatrick, K. Gregory-Evans, M. Bhatia, and H. Sheardown, "NIPAAm Based Cell Delivery Scaffolds for Posterior Segment Therapeutics," *Investigative Ophthalmology & Visual Science*, vol. 54, no. 15, pp. 4627-4627, 2013.

[24] D. Das et al., "Stimulus-Responsive, Biodegradable, Biocompatible, Covalently Cross-Linked Hydrogel Based on Dextrin and Poly(N-isopropylacrylamide) for in Vitro/in Vivo Controlled Drug Release," *ACS Appl Mater Interfaces*, vol. 7, no. 26, pp. 14338-51, Jul. 8, 2015, doi: 10.1021/acsami.5b02975.

[25] J.-Y. Lai, "Biodegradable in situ gelling delivery systems containing pilocarpine as new antiglaucoma formulations: effect of a mercaptoacetic acid/N-isopropylacrylamide molar ratio," *Drug Design, Development and Therapy*, vol. 7, p. 1273, 2013.

[26] J. Y. Lai and A. C. Hsieh, "A gelatin-g-poly(N-isopropylacrylamide) biodegradable in situ gelling delivery system for the intracameral administration of pilocarpine," *Biomaterials*, vol. 33, no. 7, pp. 2372-87, March 2012, doi: 10.1016/j.biomaterials.2011.11.085.

[27] L. J. Luo and J. Y. Lai, "Epigallocatechin Gallate-Loaded Gelatin-g-Poly(N-Isopropylacrylamide) as a New Ophthalmic Pharmaceutical Formulation for Topical Use in the Treatment of Dry Eye Syndrome," *Sci Rep*, vol. 7, no. 1, p. 9380, Aug. 24, 2017, doi: 10.1038/s41598-017-09913-8.

[28] Y. Yu, X. Chang, H. Ning, and S. Zhang, "Synthesis and characterization of thermoresponsive hydrogels cross-linked with chitosan," *Central European Journal of Chemistry*, vol. 6, no. 1, pp. 107-113, 2008.

[29] Y. Yu, Y. Li, C. Zhu, and L. Liu, "Synthesis and characterization of temperature-sensitive and biodegradable hydrogel based on N-isopropylacrylamide," *Open Chemistry*, vol. 8, no. 2, pp. 426-433, 2010.

[30] J. Y. Lai and L. J. Luo, "Chitosan-g-poly(N-isopropylacrylamide) copolymers as delivery carriers for intracameral pilocarpine administration," *Eur J Pharm Biopharm*, vol. 113, pp. 140-148, April 2017, doi: 10.1016/j.ejpb.2016.11.038.

[31] L. J. Luo, D. D. Nguyen, and J. Y. Lai, "Benzoic acid derivative-modified chitosan-g-poly(N-isopropylacrylamide): Methoxylation effects and pharmacological treatments of Glaucoma-related neurodegeneration," *J Control Release*, vol. 317, pp. 246-258, Jan. 10, 2020, doi: 10.1016/j.jconrel.2019.11.038.

[32] D. D. Nguyen, L. J. Luo, S. J. Lue, and J. Y. Lai, "The role of aromatic ring number in phenolic compound-conjugated chitosan injectables for sustained therapeutic antiglaucoma efficacy," *Carbohydr Polym*, vol. 231, p. 115770, Mar. 1, 2020, doi: 10.1016/j.carbpol.2019.115770.

[33] H. J. Davidson and V. J. Kuonen, "The tear film and ocular mucins," *Veterinary ophthalmology*, vol. 7, no. 2, pp. 71-77, 2004.

[34] R. S. Dave, T. C. Goostrey, M. Ziolkowska, S. Czerny-Holownia, T. Hoare, and H. Sheardown, "Ocular drug delivery to the anterior segment using nanocarriers: A mucoadhesive/mucopenetrative perspective," *Journal of Controlled Release*, 2021.

[35] C. Federer, M. Kurpiers, and A. Bernkop-Schnürch, "Thiolated chitosans: a multi-talented class of polymers for various applications," *Biomacromolecules*, vol. 22, no. 1, pp. 24-56, 2020.

[36] S.-J. Hwang, H. Park, and K. Park, "Gastric retentive drug-delivery systems," *Critical Reviews™ in Therapeutic Drug Carrier Systems*, vol. 15, no. 3, 1998.

[37] C. Menzel, M. Jelkmann, F. Laffleur, and A. Bernkop-Schnürch, "Nasal drug delivery: design of a novel mucoadhesive and in situ gelling polymer," *International journal of pharmaceutics*, vol. 517, no. 1-2, pp. 196-202, 2017.

[38] B. M. Boddupalli, Z. N. Mohammed, R. A. Nath, and D. Banji, "Mucoadhesive drug delivery system: An overview," *Journal of advanced pharmaceutical technology & research*, vol. 1, no. 4, p. 381, 2010.

[39] R. Shaikh, T. R. R. Singh, M. J. Garland, A. D. Woolfson, and R. F. Donnelly, "Mucoadhesive drug delivery systems," *Journal of Pharmacy and Bioallied Sciences*, vol. 3, no. 1, p. 89, 2011.

[40] I. A. Sogias, A. C. Williams, and V. V. Khutoryanskiy, "Why is chitosan mucoadhesive?," *Biomacromolecules*, vol. 9, no. 7, pp. 1837-1842, 2008.

[41] J. C. Cuggino, L. I. Tártara, L. M. Gugliotta, S. D. Palma, and C. I. A. Igarzabal, "Mucoadhesive and responsive nanogels as carriers for sustainable delivery of timolol for glaucoma therapy," *Materials Science and Engineering: C*, vol. 118, p. 111383, 2021.

[42] A. Sosnik et al., "Mucoadhesive thermo-responsive chitosan-g-poly (N-isopropylacrylamide) polymeric micelles via a one-pot gamma-radiation-assisted pathway," *Colloids and Surfaces B: Biointerfaces*, vol. 136, pp. 900-907, 2015.

[43] X. Zhu, J. DeGraaf, F. Winnik, and D. Leckband, "pH-dependent mucoadhesion of a poly (N-isopropylacrylamide) copolymer reveals design rules for drug delivery," *Langmuir*, vol. 20, no. 24, pp. 10648-10656, 2004.

[44] E. Baloglu, S. Y. Karavana, Z. A. Senyigit, and T. Guneri, "Rheological and mechanical properties of poloxamer mixtures as a mucoadhesive gel base," *Pharmaceutical development and technology*, vol. 16, no. 6, pp. 627-636, 2011.

[45] J. Y. Chang, Y.-K. Oh, H.-g. Choi, Y. B. Kim, and C.-K. Kim, "Rheological evaluation of thermosensitive and mucoadhesive vaginal gels in physiological conditions," *International journal of pharmaceutics*, vol. 241, no. 1, pp. 155-163, 2002.

[46] S. B. D. S. Ferreira, J. B. Da Silva, F. B. Borghi-Pangoni, M. V. Junqueira, and M. L. Bruschi, "Linear correlation between rheological, mechanical and mucoadhesive properties of polycarbophil polymer blends for biomedical applications," *Journal of the mechanical behavior of biomedical materials*, vol. 68, pp. 265-275, 2017.

[47] A. Bernkop-Schnürch, V. Schwarz, and S. Steininger, "Polymers with thiol groups: a new generation of mucoadhesive polymers?," *Pharmaceutical research*, vol. 16, no. 6, pp. 876-881, 1999.

[48] J. Iqbal, G. Shahnaz, S Dünnhaupt, C. Müller, F. Hintzen, and A. Bernkop-Schnürch, "Preactivated thiomers as mucoadhesive polymers for drug delivery," *Biomaterials*, vol. 33, no. 5, pp. 1528-1535, 2012.

[49] Y. Cao, C. Zhang, W. Shen, Z. Cheng, L. L. Yu, and Q. Ping, "Poly(N-isopropylacrylamide)-chitosan as thermosensitive in situ gel-forming system for ocular drug delivery," *J Control Release*, vol. 120, no. 3, pp. 186-94, Jul. 31, 2007, doi: 10.1016/j.jconrel.2007.05.009.

[50] J. Colter, B. Wirostko, and B. Coats, "Finite element design optimization of a hyaluronic acid-based hydrogel drug delivery device for improved retention," *Annals of Biomedical Engineering*, vol. 46, no. 2, pp. 211-221, 2018.

[51] M. V. Fedorchak, I. P. Conner, J. S. Schuman, A. Cugini, and S. R. Little, "Long term glaucoma drug delivery using a topically retained gel/microsphere eye drop," *Scientific reports*, vol. 7, no. 1, pp. 1-11, 2017.

[52] L. Leinonen, S.-L. Joutsiniemi, M.-L. Laakso, N. Lindblom, and M. Kaski, "Automatic blink detection: a method for differentiation of wake and sleep of intellectually disabled and healthy subjects in long-term ambulatory monitoring," *Sleep*, vol. 26, no. 4, pp. 473-479, 2003.

[53] T. Saitoh, Y. Sugiura, K. Asano, and M. Hiraide, "Chitosan-conjugated thermo-responsive polymer for the rapid removal of phenol in water," *Reactive and Functional Polymers*, vol. 69, no. 10, pp. 792-796, 2009, doi: 10.1016/j.reactfunctpolym.2009.06.011.

[54] S. J. Lue, C.-H. Chen, and C.-M. Shih, "Tuning of Lower Critical Solution Temperature (LCST) of Poly(N-Isopropylacrylamide-co-Acrylic acid) Hydrogels," *Journal of Macromolecular Science, Part B*, vol. 50, no. 3, pp. 563-579, 2011, doi: 10.1080/00222341003784550.

[55] T. T. Nge, M. Yamaguchi, N. Hori, A. Takemura, and H. Ono, "Synthesis and characterization of chitosan/poly (acrylic acid) polyelectrolyte complex," *Journal of applied polymer science*, vol. 83, no. 5, pp. 1025-1035, 2002.

[56] Y. Wen et al., "A potential nanoparticle-loaded in situ gel for enhanced and sustained ophthalmic delivery of dexamethasone," *Nanotechnology*, vol. 29, no. 42, p. 425101, Oct. 19, 2018, doi: 10.1088/1361-6528/aad7da.

[57] O. Guaresti, C. Garcia-Astrain, R. H. Aguirresarobe, A. Eceiza, and N. Gabilondo, "Synthesis of stimuli-responsive chitosan-based hydrogels by Diels-Alder cross-linking 'click reaction as potential carriers for drug administration," *Carbohydr Polym*, vol. 183, pp. 278-286, Mar. 1, 2018, doi: 10.1016/j.carbpol.2017.12.034.

[58] N. Yang, Y. Wang, Q. Zhang, L. Chen, and Y. Zhao, "In situ formation of poly (thiolated chitosan-co-alkylated β-cyclodextrin) hydrogels using click cross-linking for sustained drug release," *Journal of Materials Science*, vol. 54, no. 2, pp. 1677-1691, 2018, doi: 10.1007/s10853-018-2910-3.

[59] A. Okudan and A. Altay, "Investigation of the Effects of Different Hydrophilic and Hydrophobic Comonomers on the Volume Phase Transition Temperatures and Thermal Properties of N-Isopropylacrylamide-Based Hydrogels," *International Journal of Polymer Science*, vol. 2019, pp. 1-12, 2019, doi: 10.1155/2019/7324181.

[60] M. A. Haq, Y. Su, and D. Wang, "Mechanical properties of PNIPAM based hydrogels: A review," *Mater Sci Eng C Mater Biol Appl*, vol. 70, no. Pt 1, pp. 842-855, Jan. 1, 2017, doi: 10.1016/j.msec.2016.09.081.

[61] K. Varaprasad, K. Vimala, S. Ravindra, N. N. Reddy, G. S. M. Reddy, and K. M. Raju, "Biodegradable chitosan hydrogels for in vitro drug release studies of 5-flurouracil an anticancer drug," *Journal of Polymers and the Environment*, vol. 20, no. 2, pp. 573-582, 2012.

[62] S. W. Wu, X. Liu, A. L. Miller, 2nd, Y. S. Cheng, M. L. Yeh, and L. Lu, "Strengthening injectable thermo-sensitive NIPAAm-g-chitosan hydrogels using chemical cross-linking of disulfide bonds as scaffolds for tissue engineering," *Carbohydr Polym*, vol. 192, pp. 308-316, Jul. 15, 2018, doi: 10.1016/j.carbpol.2018.03.047.

[63] S. Muralidharan, L. B. Han, Y. Ming, J. Lau, K. Sailishni, and S. Arumugam, "Simple and accurate estimation of ketotifen fumarate by RP-HPLC," *International Journal of Pharmaceutical, Chemical and Biological Sciences*, vol. 2, no. 3, pp. 392-396, 2012.

[64] M. Korogiannaki, J. Zhang, and H. Sheardown, "Surface modification of model hydrogel contact lenses with hyaluronic acid via thiol-ene "click" chemistry for enhancing surface characteristics," *Journal of Biomaterials Applications*, vol. 32, no. 4, pp. 446-462, 2017.

[65] N. Boehnke, *Degradable Hydrogels and Nanogels for the Delivery of Cells and Therapeutics*. University of California, Los Angeles, 2017.

[66] X. Huang, D. Appelhans, P. Formanek, F. Simon, and B. Voit, "Tailored synthesis of intelligent polymer nanocapsules: an investigation of controlled permeability and pH-dependent degradability," *ACS nano*, vol. 6, no. 11, pp. 9718-9726, 2012.

[67] S. Rossi, B. Vigani, M. C. Bonferoni, G. Sandri, C. Caramella, and F. Ferrari, "Rheological analysis and mucoadhesion: A 30 year-old and still active combination," *Journal of pharmaceutical and biomedical analysis*, vol. 156, pp. 232-238, 2018.

The invention claimed is:

1. A thermo-gel comprising:
   a) a polymer comprising monomers N, A and X, wherein N is N-isopropylacrylamide (NIPAAm), A is acrylic acid (AA) and X is a hydrophobic monomer; and
   b) about 1 wt % to about 5 wt % chitosan, wherein the chitosan has a weight average molecular weight of about 10 kDa to about 300 kDa,
   wherein the chitosan is covalently or ionically bonded to the acrylic acid in the polymer, and wherein the acrylic acid is incorporated throughout the polymer, and
   wherein the hydrophobic monomer (X) is selected from methyl acrylate, methyl methacrylate, ethyl acrylate, ethyl methacrylate, butyl acrylate, butyl methacrylate, isobutyl acrylate, isobutyl methacrylate, 2-ethylhexyl acrylate, tert-butyl acrylate, tert-butyl methacrylate, cyclohexyl methacrylate, phenyl methacrylate, 3-[tris(trimethylsiloxy)silyl]propyl methacrylate, pyridyl disulfide ethyl methacrylate 2-(pyridin-2-yldisulfaneyl) ethyl acrylate, N-(2-(pyridin-2-yldisulfaneyl)ethyl) methacrylamide, 3-(pyridin-2-yldisulfaneyl)propyl methacrylate, 2-(pyridin-2-yldisulfaneyl)ethyl methacrylate, 2-(2-pyridin-2-yldisulfanyl)ethyl-2-(methacrylamido)acetate and N-(3-(3-(pyridin-2-yldisulfanyl)propanamido)propyl)methacrylamide.

2. The thermo-gel of claim 1, wherein the polymer further comprises one or more additional monomers.

3. The thermo-gel of claim 2, wherein the one or more additional monomers are hydrophobic monomers.

4. The thermo-gel of claim 2, wherein the one or more additional monomers are monomers comprising a disulfide moiety.

5. The thermo-gel of claim 1, wherein the polymer comprises 60-98.5 mol % NIPAAm, 1-10 mol % AA and 0.5-30 mol % of the hydrophobic monomer X.

6. The thermo-gel of claim 2, wherein the polymer comprises 60-98.5 mol % NIPAAm, 1-10 mol % AA, 0.5-30 mol % of the hydrophobic monomer X and 0.5-30% of the one or more additional monomers.

7. The thermo-gel of claim 1, wherein the polymer has a weight average molecular weight of about 1,000 g/mol to about 1,000,000 g/mol, or about 55,000 g/mol to about 66000 g/mol or about 61,500±5300 g/mol.

8. The thermo-gel of claim 1, wherein the chitosan is covalently conjugated to the polymer.

9. The thermo-gel of claim 8, wherein the chitosan is covalently conjugated to the polymer using a coupling reagent selected from 1-ethyl-3-(3-dimethyl aminopropyl)-carbodiimide (EDC), O-(benzotriazol-1-yl)-N,N,N',N'-tetramethyluronium hexafluorophosphate (HBTU), bis(2-oxo-3-oxazolidinyl)phosphinic chloride (BOP-Cl), 2-chloro-4,6-dimethoxy-1,3,5-triazine (CDMT), (chloromethylene) dimethyliminium chloride (Vilsmeier reagent), carbonyl diimidazole (CDI), propylphosphonic anhydride, diethyl chlorophosphite and dicyclohexylcarbodiimide (DCC).

10. The thermo-gel of claim 9, wherein the coupling reagent is 1-ethyl-3-(3-dimethyl aminopropyl)-carbodiimide (EDC).

11. The thermo-gel of claim 1, wherein the thermo-gel has a lower critical solution temperature (LCST) below 34-37° C., or between about 25° C. and about 32° C.

12. The thermo-gel of claim 1, wherein the chitosan has about 50 to about 80 degree of deacetylation (DDA).

13. The thermo-gel of claim 1, further comprising one or more therapeutic agents.

14. A method of treating one or more ophthalmic conditions comprising administering an effective amount of a thermo-gel of claim 1 further comprising a therapeutically effective amount of one or more therapeutic agents to a subject in need thereof.

15. The method of claim 14, wherein the one or more ophthalmic conditions are selected from cystinosis, corneal healing, glaucoma, ophthalmic pain relief, glaucoma, allergic conjunctivitis, dry eye, infection, uveitis and post-surgical applications to increase healing.

16. The method of claim 14, wherein administration of the thermo-gel is to the inferior fornix or cul-de-sac of the eye for anterior ocular drug delivery.

17. A method of improving mucoadhesive properties of a thermo-gel of claim 1 comprising incorporating one or more additional monomers comprising a disulfide moiety into the polymer of the thermo-gel of claim 1.

18. A contact lens comprising one or more thermo-gels of claim 1.

19. A method for transdermal delivery of one or more therapeutic agents comprising administering a thermo-gel of claim 1 to the skin of a subject, wherein the thermo-gel comprises the one or more therapeutic agents.

* * * * *

UNITED STATES PATENT AND TRADEMARK OFFICE
CERTIFICATE OF CORRECTION

| | |
|---|---|
| PATENT NO. | : 12,403,197 B2 |
| APPLICATION NO. | : 17/546645 |
| DATED | : September 2, 2025 |
| INVENTOR(S) | : Sheardown et al. |

Page 1 of 1

It is certified that error appears in the above-identified patent and that said Letters Patent is hereby corrected as shown below:

In the Claims

At Claim 11, Column 34, Line 16: "a lower critical solution temperature (LCST) below 34-37°" should read --a lower critical solution temperature (LCST) below 37°--.

Signed and Sealed this
Sixth Day of January, 2026

John A. Squires
*Director of the United States Patent and Trademark Office*